United States Patent
Zamierowski

(10) Patent No.: US 9,408,956 B2
(45) Date of Patent: Aug. 9, 2016

(54) CELLULAR CONTROL AND TISSUE REGENERATION SYSTEMS AND METHODS

(75) Inventor: David S. Zamierowski, Overland Park, KS (US)

(73) Assignee: KCI Licensing, Inc., San Antonio, TX (US)

( * ) Notice: Subject to any disclaimer, the term of this patent is extended or adjusted under 35 U.S.C. 154(b) by 1246 days.

(21) Appl. No.: 13/245,677

(22) Filed: Sep. 26, 2011

(65) Prior Publication Data
US 2012/0078379 A1 Mar. 29, 2012

Related U.S. Application Data

(60) Provisional application No. 61/386,380, filed on Sep. 24, 2010.

(51) Int. Cl.
*A61F 2/02* (2006.01)
*A61M 1/00* (2006.01)
(Continued)

(52) U.S. Cl.
CPC ........ *A61M 1/0084* (2013.01); *A61F 13/00051* (2013.01); *A61F 13/00068* (2013.01); *A61F 2013/0017* (2013.01); *A61F 2013/00174* (2013.01); *A61M 1/008* (2013.01); *A61M 1/009* (2014.02); *A61M 1/0088* (2013.01); *A61M 1/0092* (2014.02); *A61M 37/00* (2013.01); *A61M 37/0092* (2013.01); *A61M 2037/0007* (2013.01)

(58) Field of Classification Search
CPC . A61M 1/008; A61M 1/0084; A61M 1/0088; A61M 1/009; A61M 1/0092; A61M 37/00; A61M 37/0092; A61M 2037/0007; A61F 13/00051; A61F 13/00068; A61F 2013/0017; A61F 2013/00174
See application file for complete search history.

(56) References Cited

U.S. PATENT DOCUMENTS

| | | | |
|---|---|---|---|
| 221,427 | A | 11/1879 | Sherman |
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 | 8/1982 |
| AU | 745271 | 12/2002 |

(Continued)

OTHER PUBLICATIONS

Merriam-Webster dictionary, definition of "furl", http://www.merriam-webster.com/dictionary/furl as accessed on Mar. 31, 2016.*

(Continued)

*Primary Examiner* — Todd J Scherbel

(57) ABSTRACT

A system for in-vivo and ex-vivo tissue regeneration and cellular control, manipulation and management includes a source of cell manipulating factors, which are administered to a therapy zone via active pressure-differential components including a pump and a controller, or pulse-waves generated passively. A plate comprising tissue or an inert, bio-compatible material is provided in the therapy zone in proximity to a fluid flow manifold and tissue scaffolding. A tissue regeneration and cellular control method includes the steps of providing a cell manipulation factor source, providing one or more factors to a therapy zone and forming a pressure wave with a mechanical component or an in-vivo pressure wave source, such as the circulatory or lymphatic system.

13 Claims, 22 Drawing Sheets

(51) Int. Cl.
  *A61M 37/00* (2006.01)
  *A61F 13/00* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. |
| 3,115,138 A | 12/1963 | McEvenny et al. |
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,981,051 A | 9/1976 | Brumlik |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,248,232 A | 2/1981 | Engelbrecht et al. |
| 4,256,109 A | 3/1981 | Nichols |
| 4,259,959 A | 4/1981 | Walker |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errade et al. |
| 4,382,441 A | 5/1983 | Svedman |
| 4,392,853 A | 7/1983 | Muto |
| 4,392,858 A | 7/1983 | George et al. |
| 4,419,093 A | 12/1983 | Deaton |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,696,301 A | 9/1987 | Barabe |
| 4,710,165 A | 12/1987 | McNeil et al. |
| 4,733,659 A | 3/1988 | Edenbank et al. |
| 4,743,232 A | 5/1988 | Kruger |
| 4,758,220 A | 7/1988 | Sundblom et al. |
| 4,775,909 A | 10/1988 | Inoue |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,976,726 A | 12/1990 | Haverstock |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,139,023 A | 8/1992 | Stanley et al. |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | Debusk et al. |
| 5,358,494 A | 10/1994 | Svedman |
| 5,383,897 A | 1/1995 | Wholey |
| 5,423,885 A | 6/1995 | Williams |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |
| 5,738,686 A | 4/1998 | Budein-Meesenburg |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |
| 6,146,423 A | 11/2000 | Cohen et al. |
| 6,159,246 A | 12/2000 | Mendes et al. |
| 6,174,306 B1 | 1/2001 | Fleischmann |
| 6,179,804 B1 | 1/2001 | Satterfield |
| 6,190,391 B1 | 2/2001 | Stubbs |
| 6,190,392 B1 | 2/2001 | Vandewalle |
| 6,203,563 B1 | 3/2001 | Fernandez |
| 6,241,747 B1 | 6/2001 | Ruff |
| 6,270,517 B1 | 8/2001 | Brotz |
| RE37,358 E | 9/2001 | Del Rio et al. |
| 6,287,316 B1 | 9/2001 | Agarwal et al. |
| 6,293,929 B1 | 9/2001 | Smith et al. |
| 6,345,623 B1 | 2/2002 | Heaton et al. |
| 6,355,215 B1 | 3/2002 | Poggie et al. |
| 6,377,653 B1 | 4/2002 | Lee et al. |
| 6,398,767 B1 | 6/2002 | Fleischmann |
| 6,430,427 B1 | 8/2002 | Lee et al. |
| 6,488,643 B1 | 12/2002 | Tumey |
| 6,493,568 B1 | 12/2002 | Bell et al. |
| 6,500,209 B1 | 12/2002 | Kolb |

(56) References Cited

U.S. PATENT DOCUMENTS

| | | | |
|---|---|---|---|
| 6,503,281 | B1 | 1/2003 | Mallory |
| 6,540,705 | B2 | 4/2003 | Norstream et al. |
| 6,553,998 | B2 | 4/2003 | Heaton et al. |
| 6,589,285 | B2 | 7/2003 | Penenberg |
| 6,620,132 | B1 | 9/2003 | Skow |
| 6,626,891 | B2 | 9/2003 | Ohmstede |
| 6,645,226 | B1 | 11/2003 | Jacobs et al. |
| 6,669,735 | B1 | 12/2003 | Pelissier |
| 6,685,681 | B2 | 2/2004 | Lockwood et al. |
| 6,695,823 | B1 | 2/2004 | Lina et al. |
| 6,695,824 | B2 | 2/2004 | Howard et al. |
| 6,726,706 | B2 | 4/2004 | Dominguez |
| 6,752,794 | B2 | 6/2004 | Lockwood et al. |
| 6,764,462 | B2 | 7/2004 | Risk et al. |
| 6,800,074 | B2 | 10/2004 | Henley et al. |
| 6,814,079 | B2 | 11/2004 | Heaton et al. |
| 6,824,533 | B2 | 11/2004 | Risk, Jr. et al. |
| 6,828,468 | B2 | 12/2004 | Ansmann et al. |
| 6,856,821 | B2 | 2/2005 | Johnson |
| 6,860,903 | B2 | 3/2005 | Mears et al. |
| 6,936,037 | B2 | 8/2005 | Bubb |
| 6,951,553 | B2 | 10/2005 | Bubb et al. |
| 6,953,480 | B2 | 10/2005 | Mears et al. |
| 6,991,643 | B2 | 1/2006 | Saadat |
| 7,105,021 | B2 | 9/2006 | Edens et al. |
| 7,108,683 | B2 | 9/2006 | Zamierowski |
| 7,381,211 | B2* | 6/2008 | Zamierowski ............... 606/216 |
| 7,494,482 | B2* | 2/2009 | Orgill et al. ................. 604/305 |
| 2002/0022861 | A1 | 2/2002 | Jacobs et al. |
| 2002/0029063 | A1 | 3/2002 | Wittmann |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2005/0043818 | A1 | 2/2005 | Bellon Caneiro et al. |
| 2007/0066945 | A1* | 3/2007 | Martin ......................... 604/313 |
| 2010/0168625 | A1* | 7/2010 | Swain et al. .................... 601/6 |

FOREIGN PATENT DOCUMENTS

| | | |
|---|---|---|
| AU | 755496 | 12/2002 |
| CA | 2005436 | 6/1990 |
| DE | 2640413 | 3/1978 |
| DE | 4306478 | 9/1994 |
| DE | 29504378 | 9/1995 |
| EP | 0100148 | 2/1984 |
| EP | 0117632 | 9/1984 |
| EP | 0161865 | 11/1985 |
| EP | 0358302 | 3/1990 |
| EP | 1018967 | 8/2004 |
| EP | 1513478 | 12/2009 |
| GB | 692578 | 6/1953 |
| GB | 2195255 | 4/1988 |
| GB | 2197789 | 6/1988 |
| GB | 2220357 | 1/1990 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | WO-80/02182 | 10/1980 |
| WO | WO-87/04626 | 8/1987 |
| WO | WO-90/10424 | 9/1990 |
| WO | WO-93/09727 | 5/1993 |
| WO | WO-94/20041 | 9/1994 |
| WO | WO-96/05873 | 2/1996 |
| WO | WO-97/18007 | 5/1997 |
| WO | WO-99/13793 | 3/1999 |

OTHER PUBLICATIONS

"Algorithm for Abdominal Wall Construction", *Plastic and Reconstructive Surgery*, (Jan. 2000),207-209.

"All Silicone Jackson Pratt Style Flat Drain", *C. Daniel Medical, Inc.*, retrieved from internet Mar. 15, 2007, http://www.cdanielmedical.com/flat-drain.html, 1-2.

"All Silicone Jackson Pratt Style Round Drain", *C. Daniel Medical, Inc.*, retrieved from internet Mar. 15, 2007, http://www.cdanielmedical.com/round-drain.html, 1-2.

"Hydrophobic Rigid Cannisters", http://www.bemishealthcare.com/docs/anisterHydrophobic; Retrieved from Internet Mar. 15, 2007, 1-1.

"NPD 1000 Negative Pressure Wound Therapy System", *Kalypto Medical*: www.kalyptomedical.com, (Sep. 2008),1-4.

"Patenee's Observations on the Oppositions", *KCI Licensing, Inc. Response to Opponents Smith & Nephew, Inc., and Paul Hartmann Aktiengesellschaft Oppositions*, EP 1513478 Wound Therapy and Tissue Treatment Management System and Method with Fluid Differentiation,(Apr. 21, 2011),1-15.

"PCT/GB95/01983", International Search Report, Nov. 23, 1995.

"PCT/GB96/02802", PCT International Examination and Search Report; Jan. 15, 1998 and Apr. 29, 1997.

"PCT/GB96/028202 International Application", PCT Written Opinion, Sep. 3, 1997.

"PCT/GB98/02713 International Applicaiton", PCT Written Opinion, Jun. 8, 1999.

"PCT/GB98/02713", PCT International Search Report, Jan. 8, 1999.

"Search Report and Written Opinion of the International Search Authority", International Applicaiton No. PCT/US06/38855 filed Oct. 3, 2006, report issued Aug. 8, 2007.

"Specific Dressing Techniques and Specialty Dressings", 25.

"V.A.C. Therapy Clinical Guidelines: A Reference Source for Clinicans", Jul. 2007.

Aktiengesellschaft, Paul H., "Opposition to EP1513478", (Sep. 16, 2010).

Ambrosio, Archel et al., "V.A.C. GranuFoam Silver Dressing a New Antimicrobial Silver Foam Dressing Specifically Engineered for Use with V.A.C. Therapy", http://silverlon.com/fda.html, retrieved from the internet Jul. 27, 2006, 1-71.

Anderson, Eric J., et al., "Design of Tissue Engineering Scaffolds as Delivery Devices for Mechanical and Mechanically Modulated Signals", *Tissue Engineering*, vol. 13, No. 10, (2007),2525-2539.

*Antibacterial Silver Wound Dressing, Bandage, Gauze and Adhesive Strips; Silverlon Woundcare Products*; retrieved from internet Jul. 27, 2006 http://www.silverlon.com/wound.htm, 1-5.

Arcand, N. et al., "Negative Pressure Wound Therapy and Its Application to Orthopaedics. Part II: Clinical Application", *Osteo Trauma Care*, (2006),254-258.

Argenta, Louis C., et al., "Vacuum-Assisted Closure: A New Method for Wound Control and Treatment: Clinical Experience", *Annals of Plastic Surgery*, vol. 38, No. 6, Jun. 1997, 563-576.

Armstrong, David G., et al., "Planter Pressure Changes Using a Novel Negative Pressure Wound Therapy Technique", *Journal of the Am. Podiatric Med. Assoc.*, vol. 94, No. 5, (Sep. 2004),456-460.

Arnljots, Bjorn et al., "Irrigation Treatment in Split-Thickness Skin Grafting of Intractable Leg Ulcers", *Scand J. Plast. Reconstr. Surg.*, 19, (Nov. 19, 1984),211-213.

Bagautdinov, N. A., "Variant of External Aspiration in the Treatment of Purulent Diseases of Soft Tissues", *Ministry of Higher and Secondary Education of the RSFSR I.N Ulyanov Chuvash State University*, Variant of External Aspiration in the Treatment of Purulent Diseases of Soft Tissues,94-96.

Baig, M. K., et al., "Percutaneous Postoperative Intra-Abdominal Abscess Drainage After Elective Colorectal Surgery", *Tech Coloproctol*, vol. 6, (2002),159-164.

Barker, Donald E., et al., "Vacuum Pack Technique of Temporary Abdominal Closure: A 7-Year Experience with 112 Patients", *The Journal Trauma: Injury, Infection and Critical Care*, vol. 48, No. 2, (Feb. 2000), 201-207.

Blackburn, II, MD, James H., "Negative-Pressure Dressings as a bolster for Skin Grafts", *Annals of Plastic Surgery*, vol. 40, No. 5, May 1998, 453-457.

Boersma, Saskia M., et al., "Photogrammetric Wound Measurement with a Three-Camera Vision System", *IAPRS*, vol. 33, (2000).

Brabmamdam, Pavan et al., "Critical Care I", *Surg. Forum Abstracts*, vol. 207, No. 3S, (Sep. 2008),S34-S35.

(56) References Cited

OTHER PUBLICATIONS

Brock, Bradford et al., "Temporary Closure of Open Abdominal Wounds: The Vacuum Pack", *The Am. Surgeon.*, vol. 61, No. 1, (Jan. 1995),30-35.
Brody, Sarah et al., "Approaches to Heart Valve Tissue Engineering Scaffold Design", *Journal of Biomedical Materials Research Part B: Applied Biomaterials*, (2006),16-43.
Burdette, Steven D., et al., "Systemic Inflammatory Response Syndrome", *eMedicine Critical Care*; http://emedicine.medscape.com/article/168943-print, (Apr. 16, 2007),1-19.
Chariker, Mark E., et al., "Effective Managment of Incisional and Cutaneous Fistulae with Closed Suction Wound Drainage", *Contemporary Surgery*, vol. 34, (Jun. 1989),59-63.
Cheboksary, "Current Problems in Modern Clinincal Surgery Interdepartmental Collection", *Ministry of Higher and Secondary Education of the RSFSR I.N. Ulyanov Chuvash State University*, (May 21, 1986),1-153.
Chinn, Steven D., et al., "Closed Wound Suction Drainage", *The Journal of Foot Surgery*, vol. 1, No. 1, (1985),76-81.
Culliford, Alfred T., "A Novel Technique for Vacuum Assisted Closure Device Application in Noncontiguous Wounds", *Journal of Plastic, Reconstructive and Aesthetic Surgery*, (2006),1-2.
Cunningham, Kim "Development of in-vitro Model to Simulate Dermal Wound Bed Interaction with Granufoam and Gauze Dressing Under Sub Atmospheric Pressure", *Micro CT Study-Test Cell Development, Report*, (Jul. 30, 2006),1-19.
Dattilo, Jr., Philip P., et al., "Medical Textiles: Applications of an Absorable Barbed Bi-directional Surgical Suture", *Journal of Textile and Apparel, Technology and Management*, vol. 2, Issue 2, Spring 2002, 1-5.
Davydov, Yu A., et al., "Bacteriological and Cytological Assessment of Vacuum Therapy of Purulent Wounds", *Vestnik Khirurgi*, Oct. 1998, 48-52.
Davydov, Yu A., et al., "Concepts for the Clinical-Biological Management of the Wound Process in the Treatment of Purulent Wounds by Means of Vacuum Therapy", *Vestnik Khirurgi*, Jul. 7, 1980, 132-136.
Davydov, Yu A., et al., "Vacuum Therapy in the Treatment of Purulent Lactation Mastitis", *Vestnik Khirurgi*, May 14, 1986, 66-70.
Dee, A. "The Successful Managment of a dehisced Surgical Wound with TNP Following Femoropopliteal Bypass", *Journal of Wound Care*, vol. 16, No. 1, (Jan. 2007),42-44.
Delalleau, Alexandre et al., "Characterization of the Mechanical Properties of Skin by Inverse Analysis Combined with the Indentation Test", *Journal of Biomechanics*, vol. 39, (2006),1603-1610.
Diridollou, S. et al., "In vivo Model of the Mechanical Properties of the Human Skin Under Suction", *Skin Research and Technology*, vol. 6, (2000),214-221.
Dubick, Michael A., et al., "Issues of Concern Regarding the Use of Hypertonic/Hyperoncotic Fluid Resuscitation of Hemorrahagic Hypotension", *Shock*, vol. 25, No. 4, (2006),321-328.
Egnell Minor, "Addition to the User's Manual Concerning Overflow Protection", *Industrigaton2, 461, 37 Trollhattan*, (Feb. 3, 1983),2.
Egnell Minor, "Egnell Minor Instruction Book, 1st Edition, 300 7502", (Feb. 1975),1-24.
Garner, Glen et al., "Vacuum-Assisted Wound Closure Provides Early Fascial Reapproximation in Trauma Patients with Open Abdomens", *The Am. Journ. Surg*, vol. 182, (2001),630-638.
Gemmiti, Christopher V., et al., "Fluid Flow Increases Type II Collagen Deposition and Tensile Mechanical Properties in Bioreactor-Grown Tissue-Engineered Cartilage", *Tissue Engineering*, vol. 12, No. 3, (2006),469-479.
Greer, S. E., et al., "The Use of Subatmospheric Pressure Dressing Therapy to Close Lymphocutaneous Fistulas of the Groin", *British Journal of Plastic Surgery*, (2000), 53, Article No. BJPS2000, 3360,484-487.
Gupta, Subhas et al., "Guidelines for Managing Pressure Ulcers with Negative Pressure Wound Therapy", *Supplement to Advances in Skin and Wound Care*, vol. 17, Supp. 2, (Nov. 2004),1-16.

Herte, Mary C., et al., "Comparative Wound Healing in Animal Subjects Using the Cuba System VS Conventional Surgical instruments", *The American Society of Plastic and Reconstructive Surgeons*, (Nov. 1978),1-19.
Jeschke, Marc G., et al., "Development of New Reconstructive Techniques: Use of Integra in Combination with Fibrin Glue and Negative-Pressure Therapy fro Reconstruction of Acute and Chronic Wounds", *Departments of General Surgery and Trauma and Reconstructive Surgery*, University of Regensburg, (Jan. 15, 2003),525-530.
Jeter, Katherine F., et al., "Managing Draining Wounds and Fistulae: New and Established Methods", *Chronic Wound Care: Health Management Publications*, (1990),240-246.
Johnson, Frank E., "An Improved Technique for Skin Graft Placement Using a Suction Drain", *Surgery, Gynecology & Obstetrics*, vol. 159, (Dec. 1984),585-586.
Kaplan, Mark et al., "Guidelines for the Management of the Open Abdomen", *Supplement to Wounds*, (Oct. 2005),1-26.
Khatyr, Fouad "Model of the Viscoelastic Behaviour of Skin in vivo and Study of Anisotropy", *Skin Research and Technology*, vol. 10, (2004),96-103.
Kostyuchenok, B. M., et al., "Vacuum Treatment in the Surgical Management of Purulent Wounds", *Vestnik Khirugi*, Sep. 1986, 18-21.
Kuznetsov, V A., et al., "Vacuum and Vacuum-Sorption Treatment of open Septic Wounds, Appendix B", *II All-Union Conference on Wounds and Wound Infections: Presentation Abstracts* Moscow, U.S. S.R., (Oct. 29, 1986),91-92.
Kwan, Michael K., et al., "A Structural Model to Describe the Nonlinear stress-Strain Behavior for Parellel-Fibered Collagenous Tissues", *Journal of Biomechanical Engineering*, vol. 111, (Nov. 1989),361-363.
Lago, Natalia et al., "Neurobiological Assessment of Regenerative Electrodes for Bidirectional Interfacing Injured Peripheral Nerves", *IEEE Transactions on Biomedical Engineering*, vol. 54, No. 6, (Jun. 2007),1129-1137.
Laskin, Richard S., "Minimally Invasive Total Knee Replacement Using a Mini-Mid Vastus Incision Technique and Results", *Surgical Technology Internatinal*, vol. 13, (2004),231-238.
Latenser, Barbara A., et al., "A Pilot Study Comparing Percutaneous Decompression with Decompressive Laparotomy for Acute Abdominal Compartment Syndrome in Thermal Injury", *Journal of Burn Care & Rehab.*, vol. 23, No. 3, (May/Jun. 2002),190-195.
Lavery, Lawrence A., et al., "Emerging Concepts with VAC Therapy", *Podiatry Today*, vol. 20, (Jul. 1, 2007),1-6.
Letsou, M.D., George V., et al., "Stimulation of Adenylate Cyclase Activity in Cultured Endothelial Cells Subjected to Cyclic Stretch", *Journal of Cardiovascular Surgery*, 31, 1990, 534-539.
Manwaring, Michael E., et al., "Characterization of Rat Meningeal Cultures on Materials of Differing Surface Chemistry", *Biomaterials*, vol. 22, (2001).
Manwaring, Michael E., et al., "Contact Guidance Induced Organization of Extracellular Matrix", *Biomaterials*, vol. 25, (2003),3631-3638.
Masters, John "Letter to the Editor", *British Journal of Plastic Surgery*, vol. 51(3), 1998; *Elsevier Science/The British Association of Plastic Surgeons*, UK, 267.
Mendez-Eastman, RN, Susan "When Wounds Won't Heal", *RN*, Jan. 1998, vol. 61(1), *Medical Economics Company, Inc.*, Montvale, NJ, USA, 20-24.
Mercier, Nichole R., et al., "Poly(lactide-co-glycolide) microspheres as a moldable scaffold for Cartilage Tissue Engineering", *Biomaterials*, vol. 26, (2005),1945-1952.
*Merriam Webster Online Dictionary*; http: www.merriam-webster.com/dictionary/occlude_http: www.merriam-webster.com/dictionary/occlusion retrieved from internet Mar. 4, 2008.
Meyer, P. et al., "A New Abdominal Drain for Overflowing Lavage in Instances of Severe Pancreatitis with Persistent Peritonel Contamination", *Surgery, Gynecology & Obstetrics*, vol. 165, (Sep. 1987).
Meyer, Willy et al., "Selections from Bier's Hyperemic Treatment in Surgery Medicine, and the Specialties: A Manual of Its Practical Application", *W.B. Sunders Co.*, 2 Ed., (1909),17-25, 44-64, 90-96, 167-170, and 210-211.

(56) References Cited

OTHER PUBLICATIONS

Mikos, Antonios G., et al., "Preparation of Poly(glycolic acid) Bonded Fiber Structures for Cell Attachment and Transplantation", *Journal of Biomedical Materials Research*, vol. 27, (1993),183-189.

Miyauchi, Takayuki et al., "Repair of Incisional Hernia with Prolene Hernia System", *The Journal of Medical Investigation*, vol. 50, p. 108-111, 2003; received for publication Aug. 8, 2002.

Morykwas, Michael J., et al., "Vacuum-Assisted Closure: A new Method for Wound Control and Treatment: Animal Studies and Basic Foundation", *Annals of Plastic Surgery*, vol. 38, No. 6, (1997),553-562.

Norman, James J., et al., "Methods for Fabrication of Nanoscale Topography for Tissue Engineering Scaffolds", *Annals of Biomedical Engineering*, vol. 34, No. 1, (Jan. 2006),89-101.

Orringer, Jay et al., "Management of Wounds in Patients with Complex Enterocutaneous Fistulas", *Surgery, Gynecology & Obstertics*, vol. 165, Jul. 1987, 79-80.

Pailler-Mattei, C. et al., "Study of Adhesion Forces and Mechanical Properties of Human Skin in vivo", *J. Adhesion Sci. Technol.*, vol. 18, No. 15-16, (2004),1739-1758.

Pfister, Bryan J., et al., "Neural Engineering to Produce in Vitro Nerve Constructs and Neurointerface", *Neurosurger*: www.neurosurgery-online.com, (2007),137-142.

Poritz, Lisa S., et al., "Percutaneous Drainage and Ileocolectomy for Spontaneous Intraabdominal Abscess in Chrohn's Disease", *J. Gas. Surg.*, vol. 11, (Jan. 19, 2007),204-207.

Puyana, "Resuscitation of Hypovolemic Shock", *Textbook of Critical Care*, 5th Ed., Ch. 229, (2005),1933-1943.

Reckard, Justin M., et al., "Management of Intraabdominal Hypertension by Percutaneous Catheter Drainage", *JVIR*, vol. 16, No. 7, (Jul. 2005),1019-1021.

Robledo-Ogazon, Felipe et al., "Using the Vacuum Assisted Closure System VAC in the Treatment of Infected Surgical Wounds. Clinical Experience", *madigraphic Artemisa*, vol. 74, No. 2, (Mar.-Apr. 2006),107-113

Sachlos, E. et al., "Making Tissue Engineering Scaffolds WOrk. Review on the Application of Solid Freeform Fabrication Technology to the Production of Tissue Engineering Scaffolds", *European Cells and Materials*, vol. 5, (2003),29-40.

Safronov, A. A., "Vacuum Therapy of Trophic Ulcer of the Lower Leg with Simultaneous Autoplasty of the Skin", *Ministry of Public Health of the USSR*, (1967),1-50.

Schein, M. et al., "The 'sandwich technique' Management of the Open Abdomen", *Br. J. Surg.*, vol. 73, (May 1986),369-370.

Segvich, Sharon et al., "Uniform Deposition of Protein Incorporated Mineral Layer on Three-Dimensional Porous Polymer Scaffolds", *Journal of Biomedical Materials Research Part B: Applied Biomaterials 84B(2)*: <http://hdl.handle.net/2027.42/57926>, (May 8, 2007),340-349.

Sherck, John et al., "Covering the "Open Abdomen": A Better Technique", *The American Surgeon*, vol. 64, (Sep. 1998).

Shimko, Daniel A., et al., "Effect of Porosity on the Fluid Flow Characteristics and Mechanical Properties of Tantalum Scaffolds", *Journal of Biomedical Materials Research, Part B, Applied Biomaterials*, (Sep. 24, 2004),315-324.

Smith & Nephew, Inc. Opposition against EP 1,513,478, (Sep. 16, 2010).

Solovev, V. A., et al., "The Method of Treatment of Immature External Fistulas in the Upper Gastrointestinal Tract", *S.M. Kirov Gorky State Medical Institute*, (1987),1-20.

Solovev, Vyacheslav A., "Treatment and Prevention of Suture Failures After Gastric Resection", *S.M. Kirov Gorky State Medical Institute*, (1988),1-55.

Svedman, Pal "A Dressing Allowing Continuous Treatment of a Biosurface", *IRCS Medical Science: Biomedical Technology; Clinical Medicine; Surgery and Transplantation*, (Jul. 1979),221.

Svedman, Pal "Irrigation Treatment of Leg Ulcers", *The Lancet*, vol. 322, Issue 8349, (Sep. 3, 1983),532-534.

Svedman, Pal et al., "A Dressing System Providing Fluid Supply and Suction Drainage Used for Continuous or Intermittent Irrigation", *Annals of Plastic Surgery*, vol. 17, No. 2, (Aug. 1986),125-133.

Takahashi, Kazutoshi et al., "Induction of Pluripotent Stem Cells from Mouse Embryonic and Adult Fibroblast Cultures by Defined Factors", *Cells*, vol. 126, (Aug. 25, 2006),663-676.

Tan, S. D., et al., "Inhibition of Osteocyte Apoptosis by Fluid Flow is Mediated by Nitric Oxide", *Biochemical and Biophysical Research Communications*, vol. 369, Issue 4, (May 16, 2008),1150-1154.

Tan, S. D., et al., "Osteocytes Subjected to Fluid Flow Inhibit Osteoclast Formation and Bone Resorption", *Bone*, vol. 4, (Jul. 27, 2007),745-751.

Tennant, C. E., "The Use of Hyperemia in the Postoperative Treatment of Lesions of the Extremities and Thorax", *Jour. A.M.A.*, (May 8, 1915),1548-1549.

Timmenga, E. J. F., et al., "The Effect of Mechanical Stress on Healing Skin Wounds: An Experimental Study of Rabbits Using Tissure Expansion", *British Journal of Plastic Surgery*, vol. 44, (1991),514-519.

Tribble, David E., "An Improved Sump Drain-Irrigation Device of Simple Construction", *Arch. Surg.*, vol. 105, (Sep. 1972),511-513.

Venturi, Mark L., et al., "Mechanisms and CLinical Applications of the Vacuum-Assisted Closure (VAC) Device", *Am. J. Clin. Dermatol.*, vol. 6 (3), (2005),185-194.

Walsh, Jennifer F., et al., "Directional Neurite Outgrowth is Enhanced by Engineered Meningeal Cell-Coated Substrates", *Tissue Engineering*, vol. 11, No. 7/8, Mary Ann Liebert, Inc., (2005),1085-1095.

Wilkes, R. et al., "3D Strain Measurement in Soft Tissue: Demonstration of Novel Inverse Finite Element Model Algorithm on MicroCT Images of a Tissue Phantom Exposed to Negative Pressure Wound Therapy", *Journal of the Mechanical Behavior of Biomedical Materials*, (Nov. 5, 2008),1-16.

Yusupov, Yu N., et al., "Active Wound Drainage", *Vestnik Khirurgi*, vol. 138, Issue 4, 1987, 42-46.

Zivadinovic, Gorica et al., "Vacuum Therapy in the Treatment of Peripheral Blood Vessels", *Conference Papers of the 5th Timok Medical Days, Timok Medical Journal, Majdanpek, Copy and Certified Translation*, (1986),161-164.

\* cited by examiner

CELLULAR CONTROL AND TISSUE REGENERATION SYSTEMS AND METHODS

CROSS-REFERENCE TO RELATED APPLICATION

This application claims priority in U.S. provisional patent application Ser. No. 61/386,380, filed Sep. 24, 2010, which is incorporated herein by reference.

BACKGROUND OF THE INVENTION

1. Field of the Invention

The present invention relates generally to tissue repair, regeneration and engineering, cellular management devices and methods, and in particular to internal implantable and external surface-mount tissue generative devices accommodating cellular manipulative influence factors, which collectively can be introduced into and applied to tissue generation zones.

2. Description of the Related Art

In the medical field, which is broadly defined to include medicine, dentistry, veterinary medicine, etc., tissue reconstruction, closure, healing and repair are important aspects of many medical procedures. Such broad intentions generally involve control and manipulation at the cellular level, including the application of various influence factors known to signal cells to grow, reproduce, migrate, align and otherwise respond positively. Applying properly indicated influence factors, including pharmacological, chemical, antimicrobial, electromagnetic force (EMF), pressure differential (negative and positive), bioengineered cells for seeding, thermal energy, acoustic energy (e.g., ultrasound), mechanical and other influence factors, has been shown to significantly improve patient outcomes across a wide range of medical conditions and treatment procedures.

The prior art includes technologies and methodologies for positively influencing cellular migration and regeneration. For example, the Zamierowski U.S. Pat. No. 4,969,880; U.S. Pat. No. 5,100,396; U.S. Pat. No. 5,261,893; U.S. Pat. No. 5,527,293; and U.S. Pat. No. 6,071,267 are incorporated herein by reference and disclose the use of pressure gradients, i.e., vacuum/negative and positive pressure, to effect wound closure and fluid drainage from wounds, including surgical incision sites. Such pressure gradients can be established by applying porous foam material either internally or externally to a wound, covering same with a permeable, semi-permeable, or impervious membrane, and connecting a suction vacuum source thereto. Fluid drawn from the patient is collected for disposal. Such fluid control methodologies have been shown to achieve significant improvements in patient outcomes. Another aspect of fluid management, postoperative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external vacuum devices. Fixation of tissues in apposition can also be achieved by bolus tie-over dressings (e.g., Stent dressings), taping, strapping and (contact) casting.

Cells can be subjected to physical forces and/or chemical signals in order to achieve desired endpoints or therapy goals. For example, mechano-transduction force signal characteristics are known to influence cell behavior. Tension, compression and shear mechanical forces can be applied to encourage tissue regeneration and wound closure. Still further, electromagnetic force (EMF) is known to encourage cellular growth and closure.

Cellular movement or "migration" is an important aspect of healing. The present invention applies various forces and other influences to accomplish cell migration in order to achieve closure and healing. In order for a cell to accomplish repair of an injured tissue, it must "migrate" into the defect and replace the missing cells and/or their functions in the damaged tissue. The same property is required for tissue engineering schema. Cells must multiply and migrate into desired shapes, beds or scaffolding to create a desired engineered tissue result. The present invention addresses regenerating and repairing a wide range of tissue types in connection with a virtually unlimited range of medical treatment procedures and desired outcomes.

Heretofore, there has not been available a cellular control system and method with the advantages and features of the present invention, including the combination of inter-tissue devices with influence factors.

SUMMARY OF THE INVENTION

In the practice of one aspect of the present invention, a medical device is provided for implanting in a tissue space wherein regeneration is indicated under one or more influence factors. The implantable device can include a plate providing a differentiating barrier for controlling pressure, fluid flow, cells and other influence factors as input and output to an in-situ therapy zone, which can be internal or external or both relative to the patient. The plate can be absorbable or non-absorbable and autologous or non-autologous. Tissue regeneration/healing/repair scaffolding provides an interface between the plate and a tissue contact layer and can facilitate tissue regeneration with a matrix composition. An external cell-manipulating factor interface comprises fluid-conveying tubing, pressure (positive and negative) application components and EMF connections with the therapy zone.

BRIEF DESCRIPTION OF THE DRAWINGS

FIG. 3A shows a conduit of the cellular control system extending through an incision in the skin surface.

DETAILED DESCRIPTION OF THE PREFERRED EMBODIMENTS

I. Introduction and Environment

Figure 1:
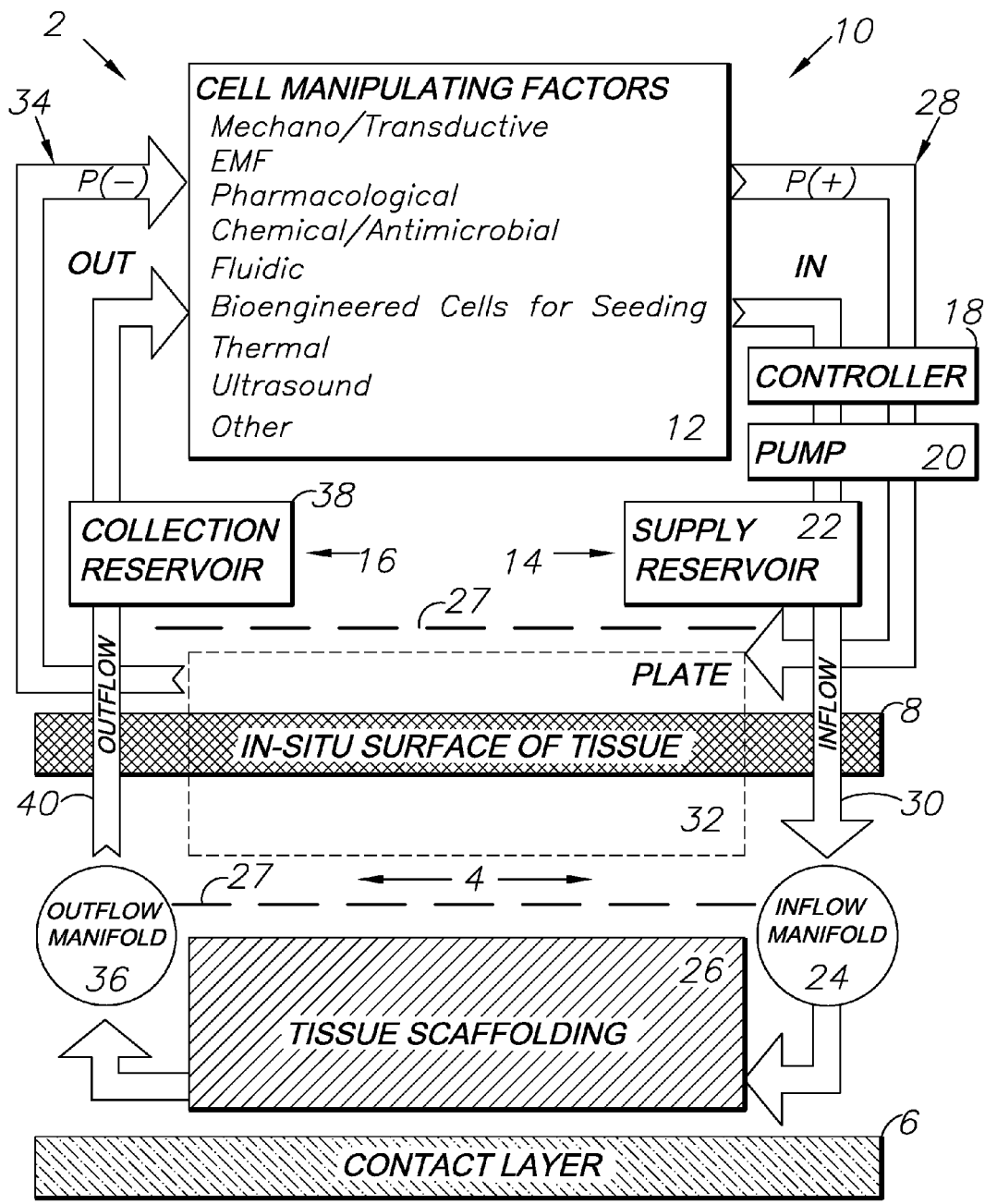
FIG. 1 is a schematic diagram of a cellular control system embodying an aspect of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. The words "horizontal" and "vertical" generally mean side-to-side and top-to-bottom, respectively. Said terminology will include the words specifically mentioned, derivatives thereof and words of a similar import.

Referring to the drawings in more detail, the reference numeral 2 generally designates a medical cellular control or tissue regeneration system embodying an aspect of the present invention. A primary intention of the cellular control system and method disclosed herein is tissue regeneration, which is broadly used to include tissue engineering, organ construction and tissue culture manufacturing. For example and without limitation on the generality of useful applications of the control system 2, a primary application disclosed herein is for controlling cellular regeneration and closure in an inter-tissue or intra-tissue space 4, which can be generally located between a contact layer 6 and an in-situ tissue surface 8, and is generally referred to as a "therapy zone." The therapy zone 4 can be located at various treatment sites in or on a patient, although typically it will be at a pathology location which is the object of a medical procedure involving cellular manipulation by one or more of the factors identified at 12, including mechano/transductive, electro-magnetic force (EMF), pharmacological, chemical/antimicrobial, fluidic, bioengineered cells for seeding, thermal energy, acoustic energy (e.g., ultrasound), osmotic, oncotic, fluid pressure differential and others.

FIG. 1 shows a general interface 10 for applying the factors 12 to the therapy zone 4. The interface 10 includes a supply or inlet side 14 and an outlet side 16. By way of example and without limitation, the inlet side 14 can include a preprogrammed, digital controller 18 connected to and controlling a pump 20, which delivers the contents of a supply reservoir 22 to an inflow manifold 24 for application to tissue regeneration/healing/repair scaffolding 26. A suitable inlet conduit subsystem 28 is provided for delivering factors 12 via the inlet side 14. The inlet side 14 also includes a positive pressure conduit 30, which can be connected to a plate structure 32 in a plate area 27 of the therapy zone 4 via the controller 18 and the pump 20. Fluid flow in the plate area 27 can be influenced and directed by the plate structure 32.

An outlet side 16 of the interface 10 includes an outlet conduit subsystem 34 connected to an outflow manifold 36 from the scaffolding 26 and discharging to a collection reservoir 38. A negative pressure (NP) pressure conduit 40 connects the plate structure 32 to the factors 12, which can include a negative pressure source. For example, one or more pumps 20 can be located on either or both sides of the plate structure 32.

Figure 2:
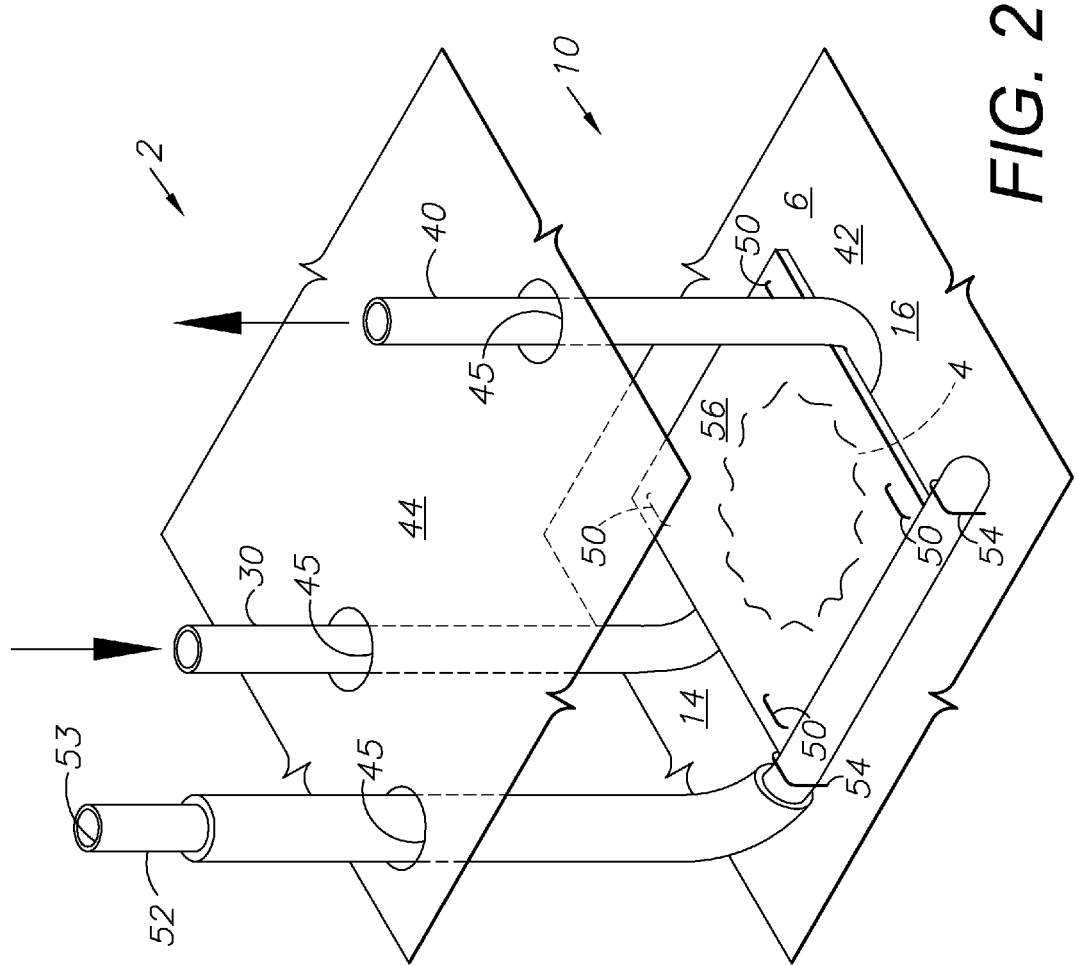
FIG. 2 is a perspective view of an inter-tissue application of the cellular control system, including a fluid/pressure interface subsystem and an endotube.

FIG. 2 shows a general configuration for the system 2 including a tissue bed 42 forming the tissue contact layer 6 and located below a skin surface 44. The inflow and outflow sides 14, 16 of the interface 10 can include respective inflow and outflow conduits 30, 40 extending through openings 45 in the skin surface 44 under the scaffolding 26 to the therapy zone 4. The scaffolding 26 can be retained in place on the tissue bed 42 by suitable anchors, such as scaffolding anchor clips 50, which can comprise staples, sutures or other suitable in-situ fasteners. An endotube 52 also extends through a skin surface opening 45 and is secured in place by endotube fasteners 54 (staples are shown) adjacent to scaffolding 56 located over the therapy zone 4. The endotube 52 is adapted for serving multiple functions, including placing and anchoring the scaffolding 56, and introducing multiple factors 12 into the therapy zone 4 via a lumen 53.

Figure 3:
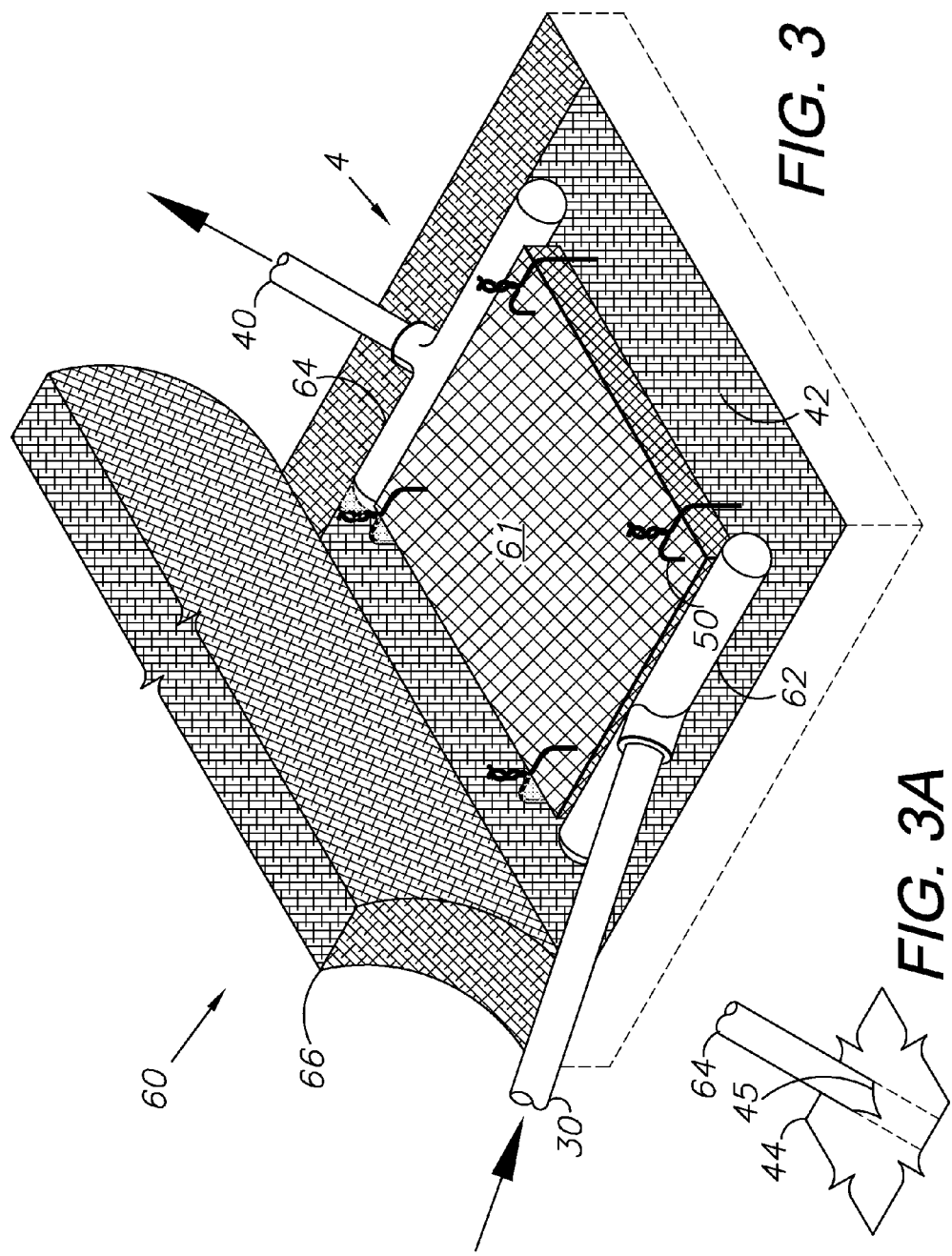
FIG. 3 shows an alternative aspect including a cover adapted for rolling or furling on an access line or conduit.
Figure 4:
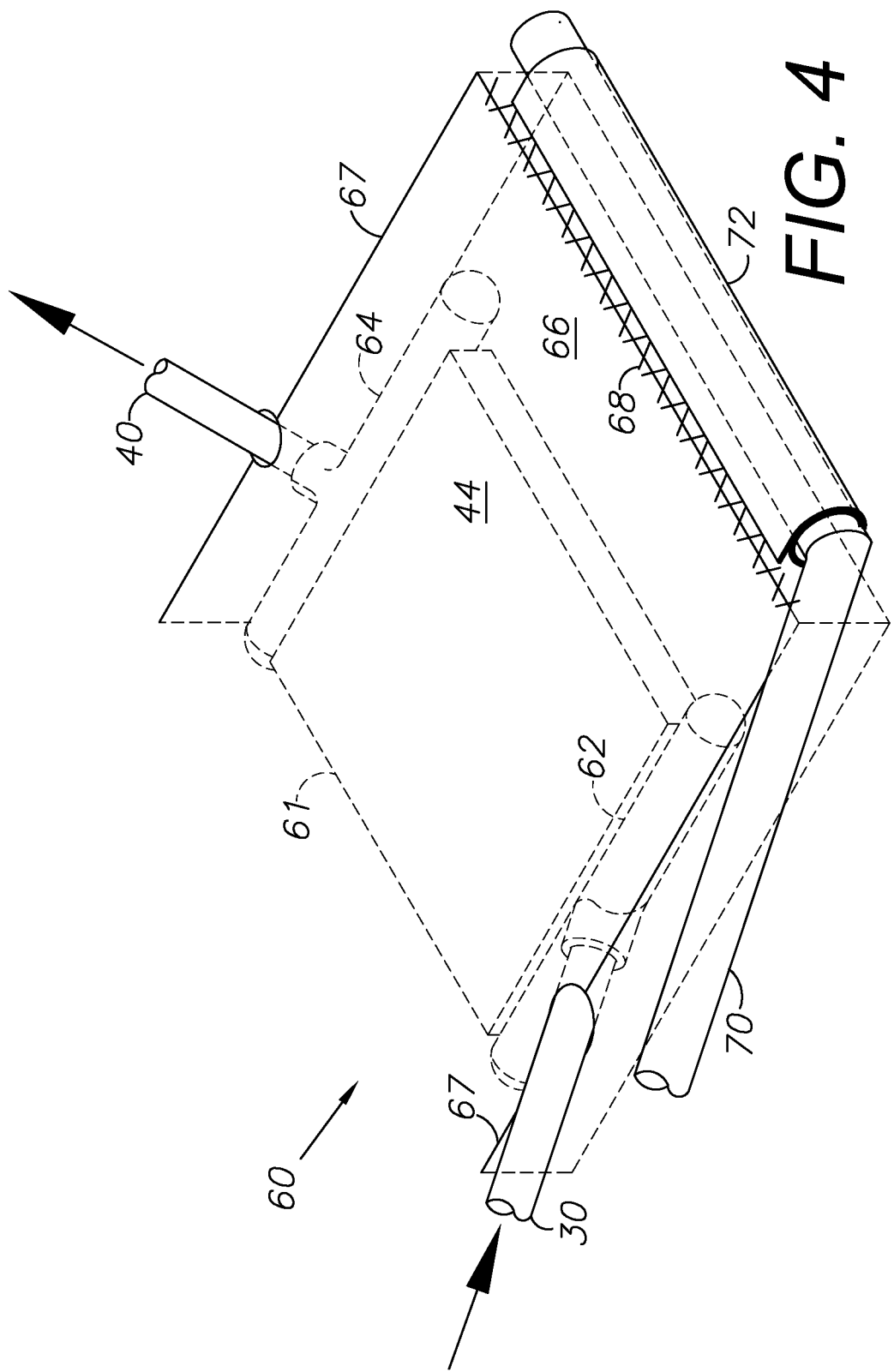
FIG. 4 shows an implanted plate and a conduit position for placing a furled cover.
Figure 5:
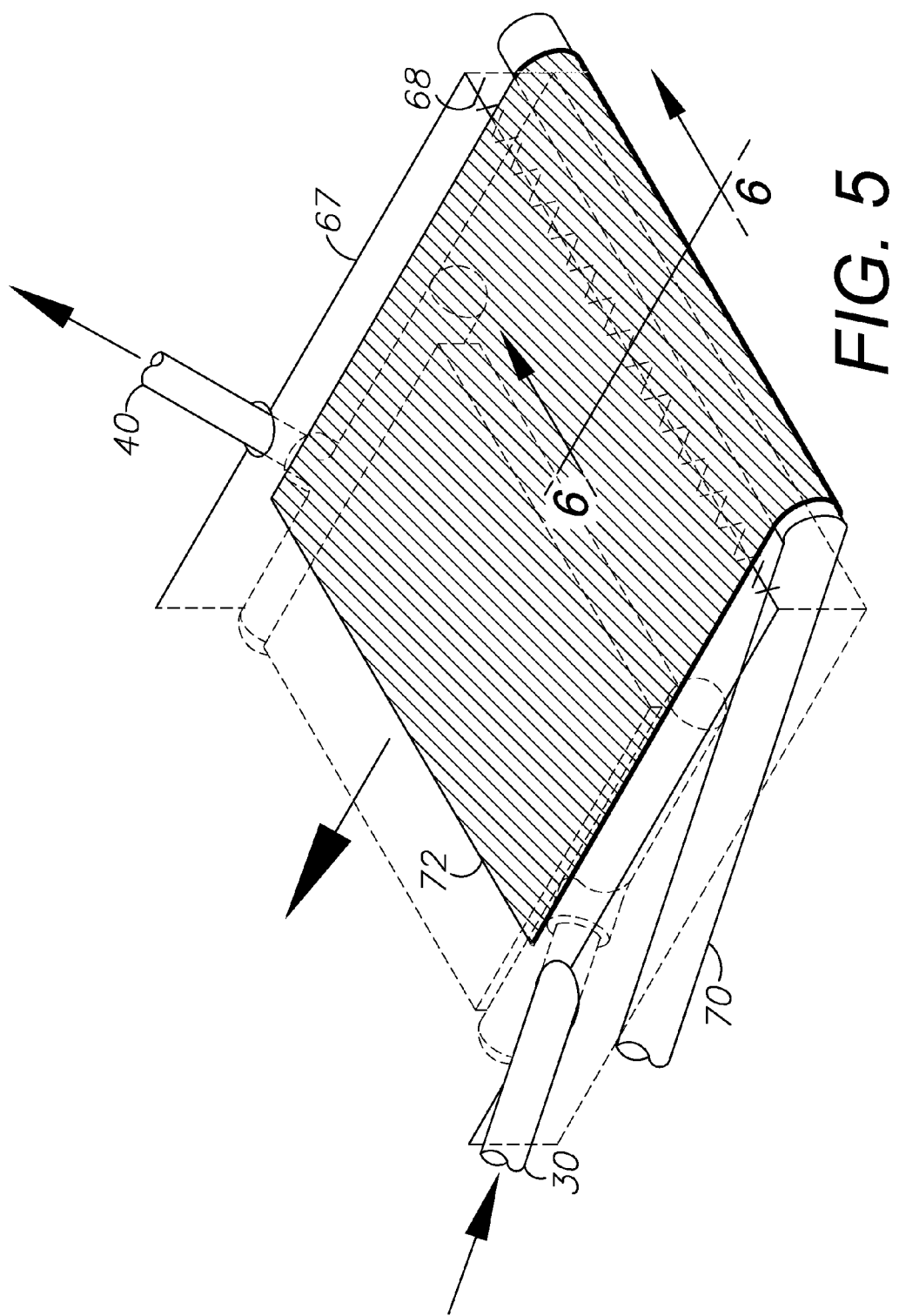
FIG. 5 shows the cover extending over a therapy zone.
Figure 6:
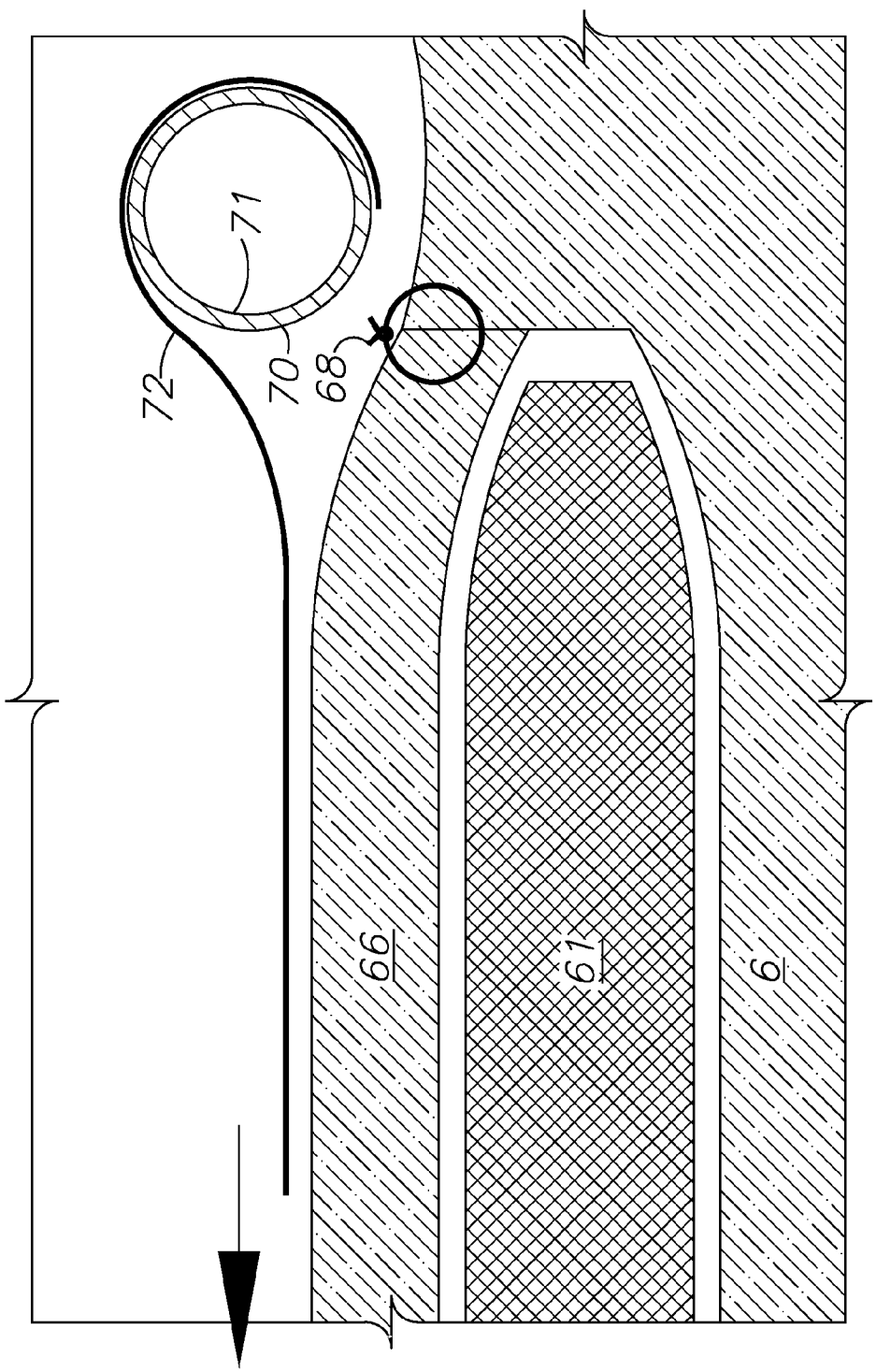
FIG. 6 is a cross-sectional view thereof taken generally along line 6-6 in FIG. 5.
Figure 7:
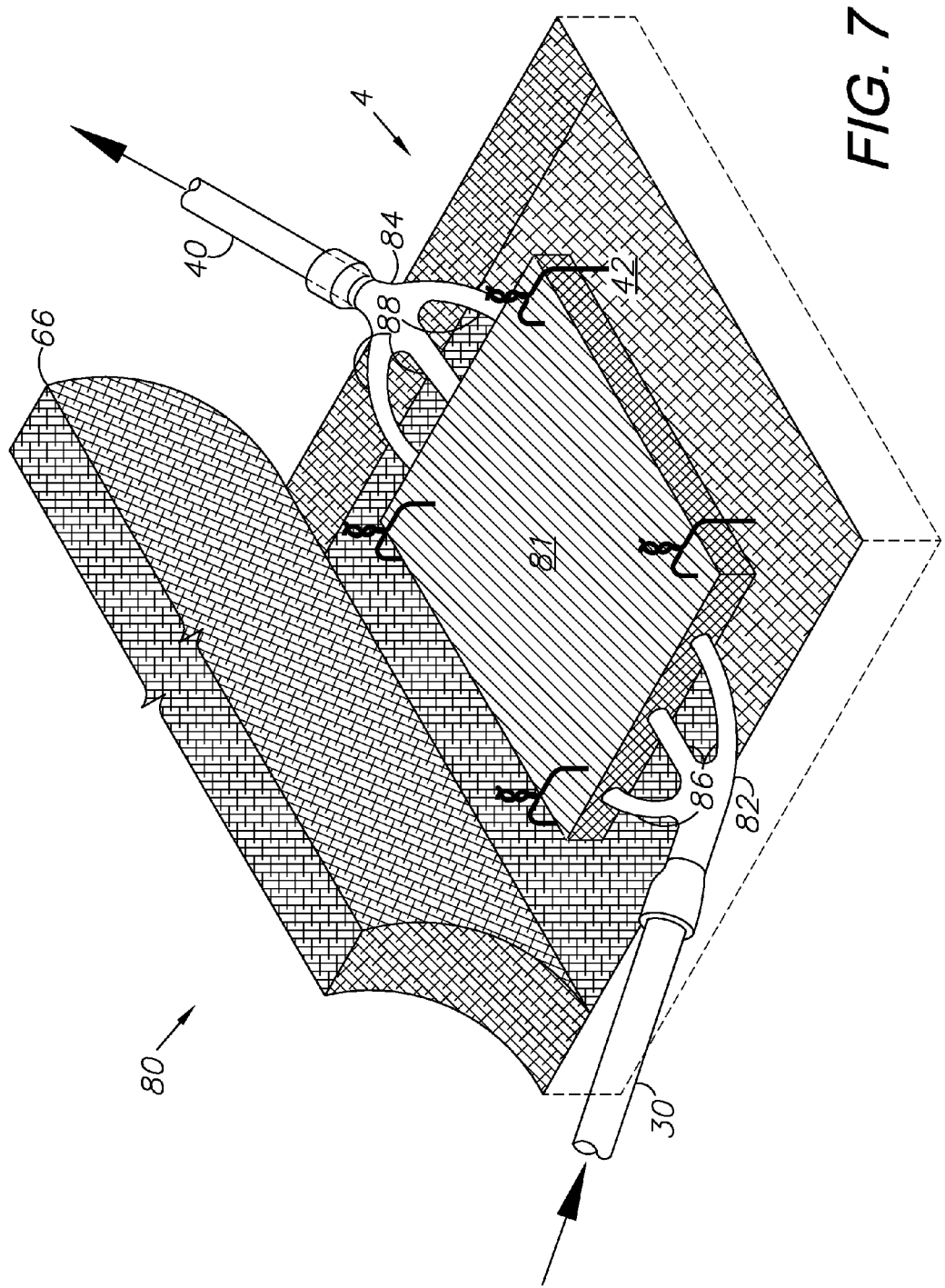
FIG. 7 shows another alternative aspect including fluid/pressure inlet and outlet conduits with manifolds engaging the plate.

FIG. 3 shows a cellular control system 60 comprising another aspect of the invention with scaffolding 61 secured to the tissue bed 42 by the scaffolding fasteners 50 and positioned between inflow and outflow manifolds 62, 64, which are connected to inflow and outflow conduits 30, 40. The manifolds 62, 64 can be perforated, porous, semi-permeable or otherwise configured for communicating factors 12 with the scaffolding 61. A tissue flap or trapdoor plate 66 can be surgically opened by the incision 67 for access to the therapy zone 4 and closed as shown in FIG. 4 with a suture line 68 with the conduits 30, 40 extending through the flap incision lines 67 on either side of the tissue flap plate 66. A furled cover 72 is wrapped around an endotube 70 with an endotube bore 71 for placement in the therapy zone 4 and can be extended to a covering position generally over the scaffolding 61 (FIG. 5). As shown in FIG. 6, the cover 72 is adapted for covering the suture line 68 during healing and can comprise various suitable wound-dressing materials, including membranes and bio-absorbable dressings.

Figure 8:
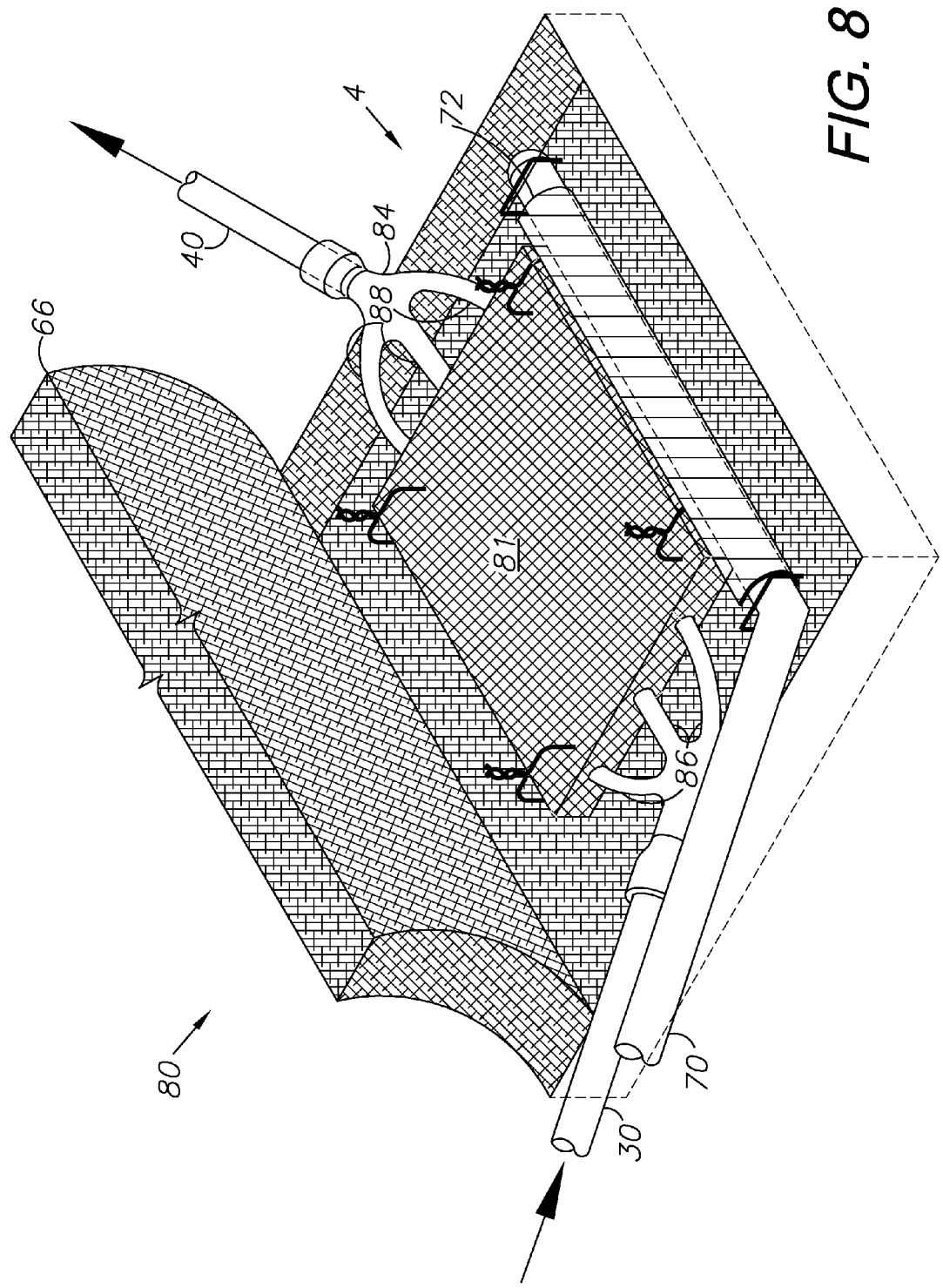
FIG. 8 shows a flexible barrier film furled on a conduit and in position for extending over the plate.
Figure 9:
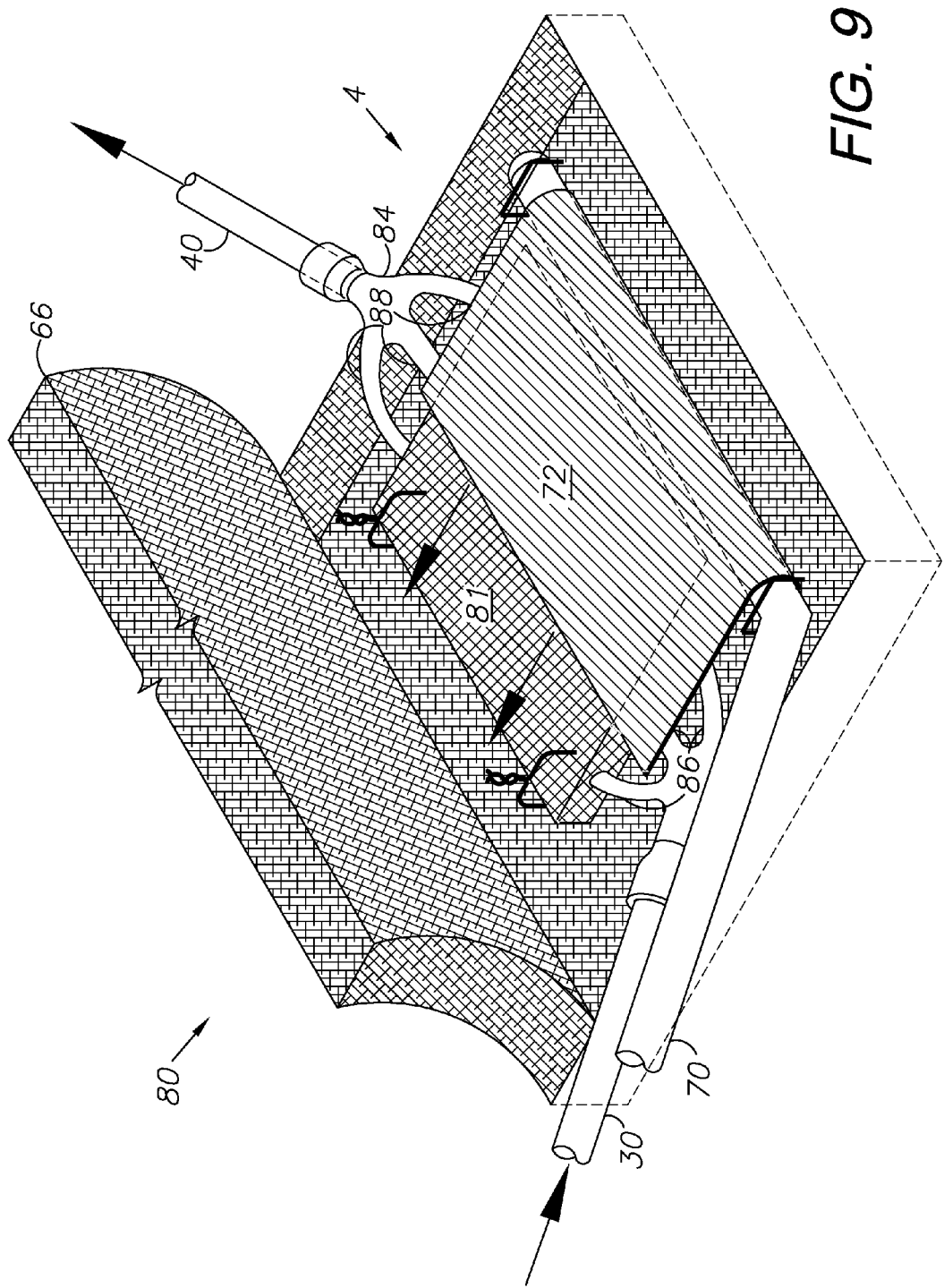
FIG. 9 shows the flexible barrier film extending over the plate.
Figure 10:
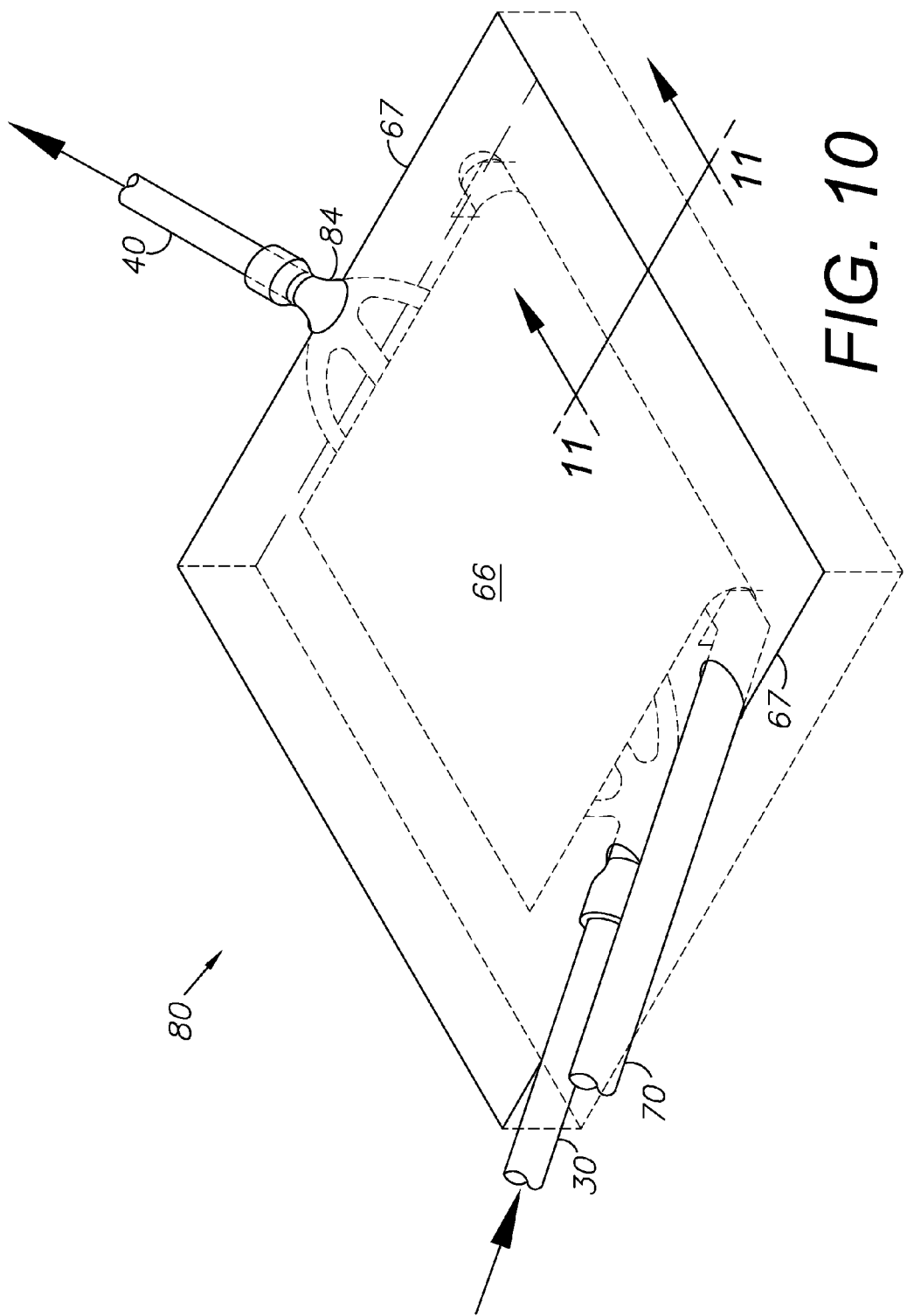
FIG. 10 shows the therapy zone closed by a tissue overlay.
Figure 11:
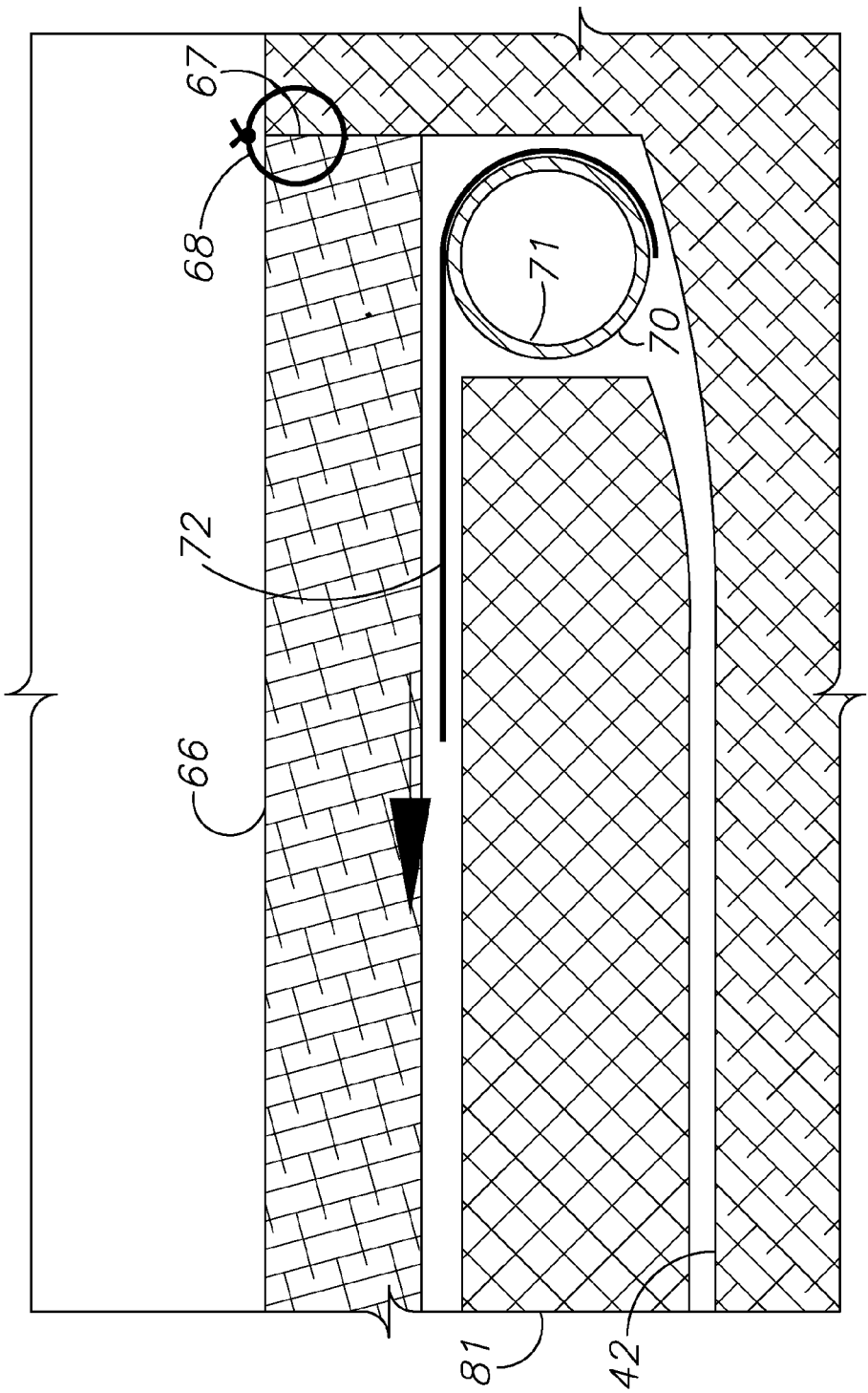
FIG. 11 is a cross-sectional view taken generally along line 11-11 and FIG. 10.

FIGS. 7-11 show another aspect of the invention comprising a cellular control system 80 with a fluid transfer element 81 inflow and outflow manifolds 82, 84 connected to conduits 30, 40 respectively and including respective manifold branches 86, 88 penetrating scaffolding 89 for communicating fluids, pressure and other factors 12. The fluid transfer element 81 can comprise open-cell foam or some other suitable fluid-transferring material. As shown in FIGS. 8, 9 and 10, an endotube 70 with a furled cover 72 can be placed within the therapy zone 4 and covered by the tissue flap 66 whereby the cellular control system 60 is substantially contained within the enclosed therapy zone 4. Within such a closed environment, the cover 72 can be unfurled and extended by rotating the endotube 70 (FIG. 11).

Figure 12:
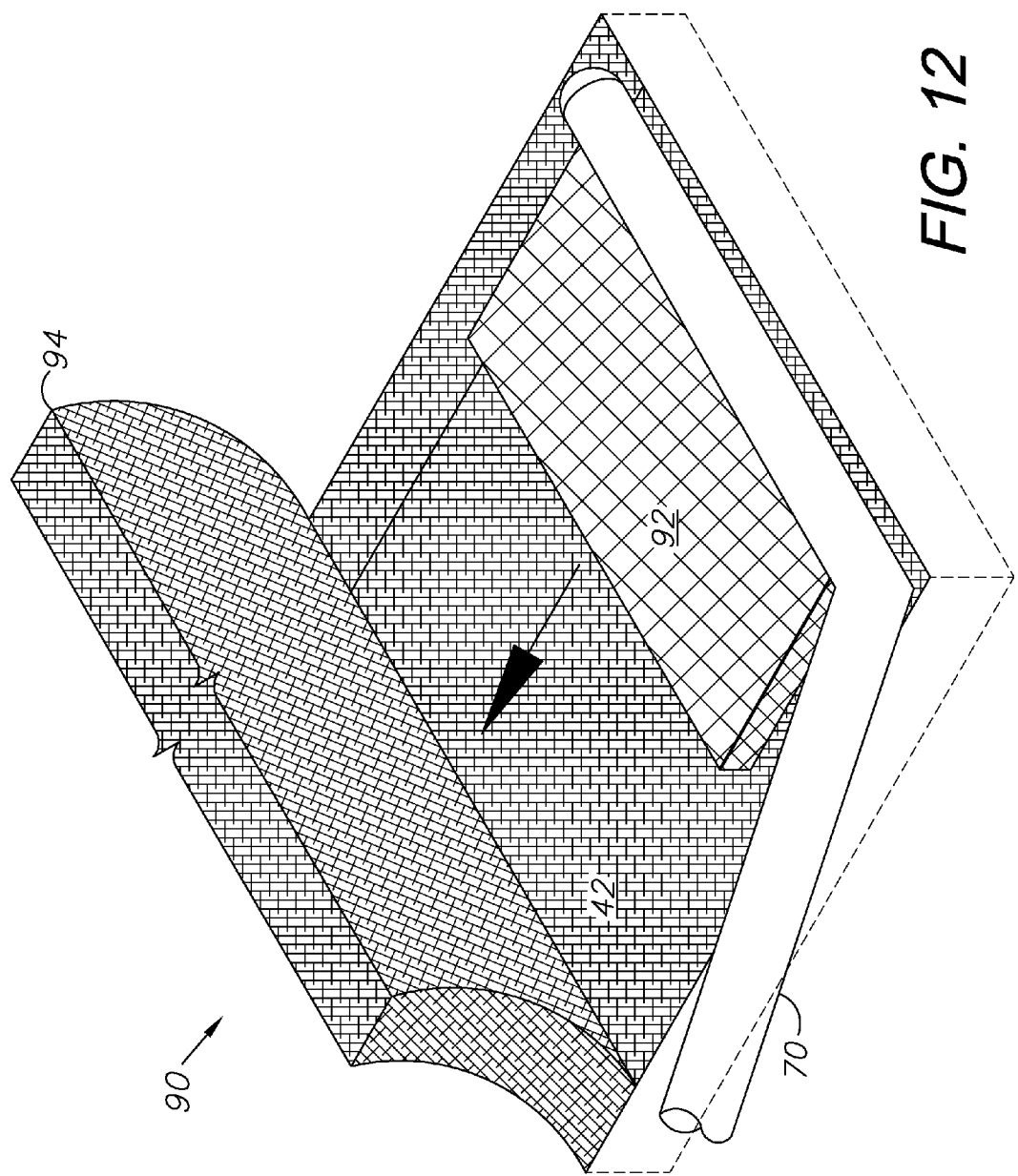
FIG. 12 shows another alternative aspect including scaffolding installed with an endotube.
Figure 13:
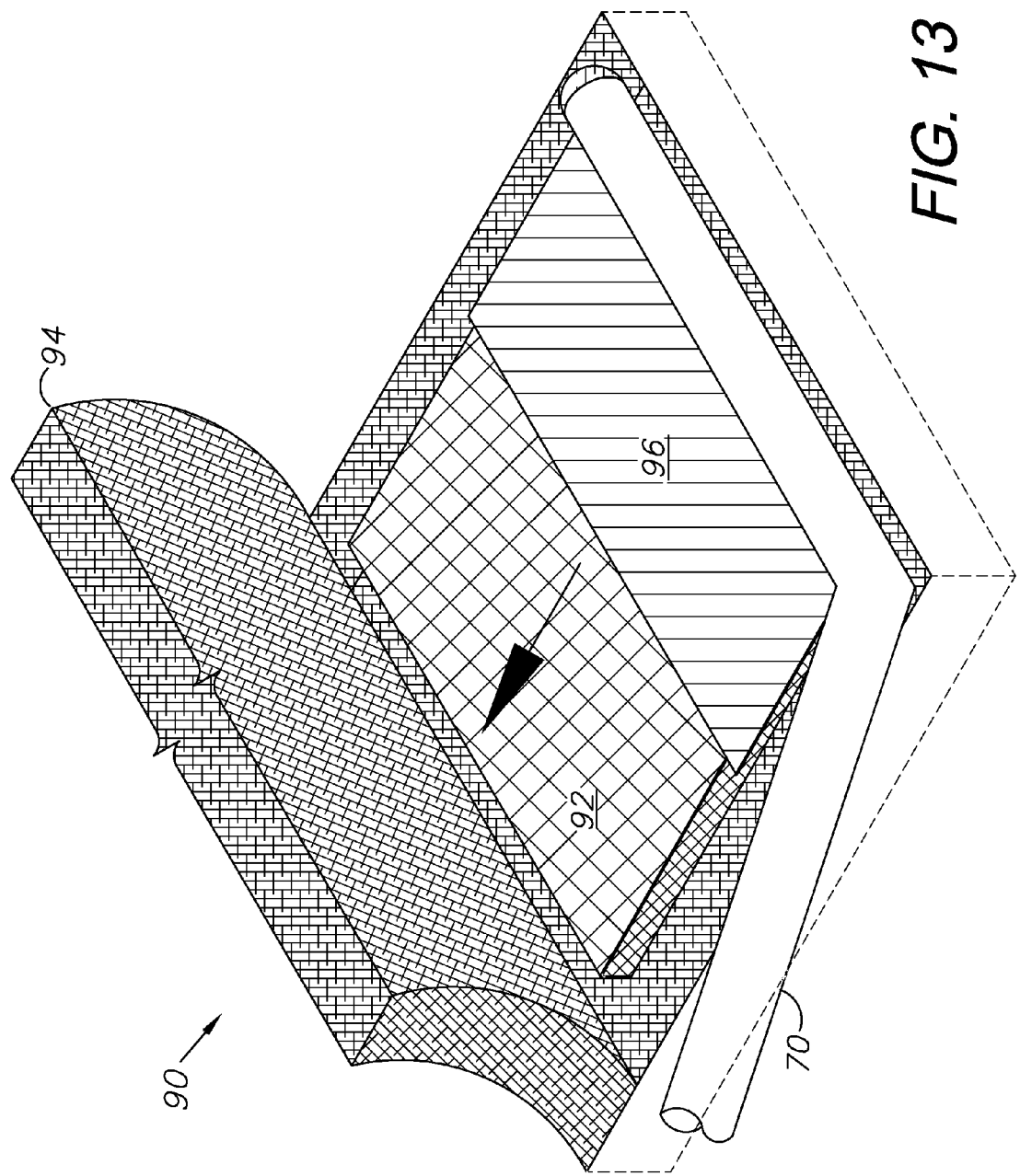
FIG. 13 shows an absorbable fabric hemostatic layer being applied over the scaffolding via the endotube.
Figure 14:
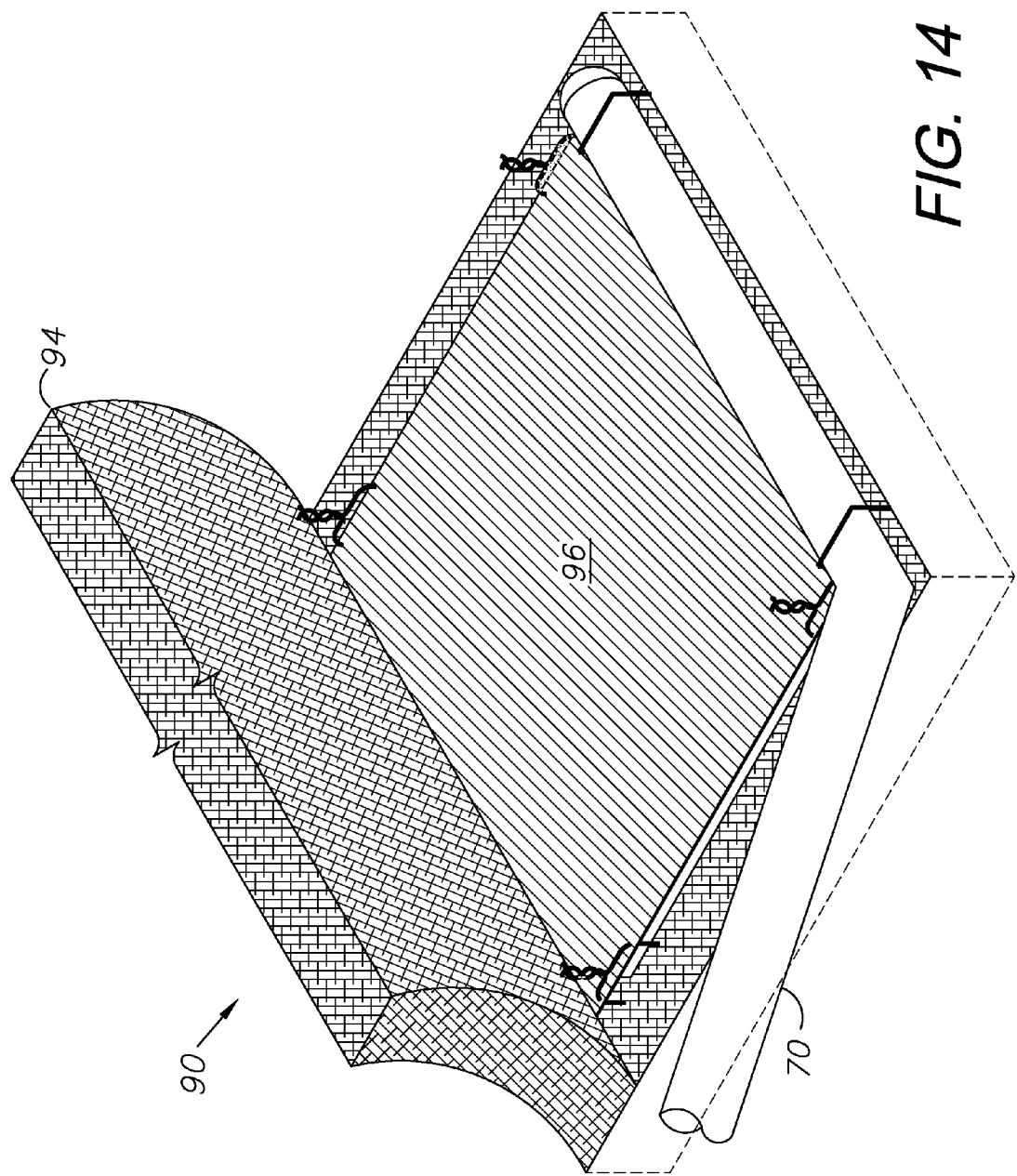
FIG. 14 shows the completed assembly of the system in the therapy zone.
Figure 15:
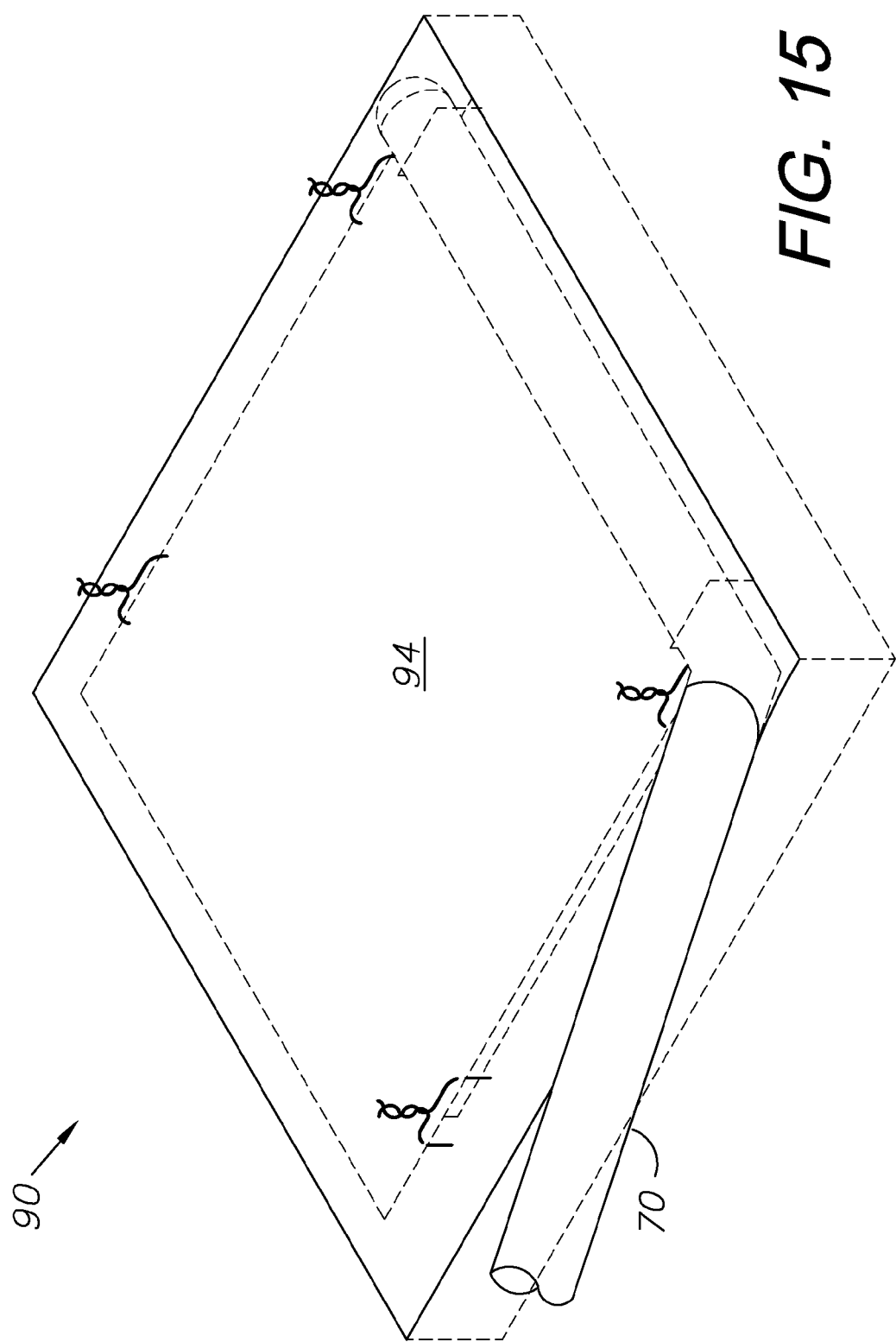
FIG. 15 shows the therapy zone covered by a tissue trapdoor plate.

FIGS. 12-17 show a cellular control system 90 comprising another aspect of the invention and including scaffolding 92 adapted for placement in the therapy zone 4 on the tissue bed 6, which can be surgically exposed by lifting a tissue flap plate or trapdoor 94. As shown in FIG. 12, the scaffolding 92 can be placed with the endotube 52, which is positioned in the therapy zone 4 and in turn positions the scaffolding 92 over the tissue bed 6. An absorbable fabric hemostatic layer 96 is extended over the scaffolding 92 as shown in FIG. 13 and is secured to the tissue bed 6 with suitable fasteners 50, such as sutures or staples. The trapdoor 94 functions as the plate in this configuration and is placed over the scaffolding 92, the endotube 52 and the fabric hemostatic layer 96, as shown in FIG. 15. The tissue flap trapdoor plate 94 can be sutured in place over the therapy zone 4.

Figure 16:
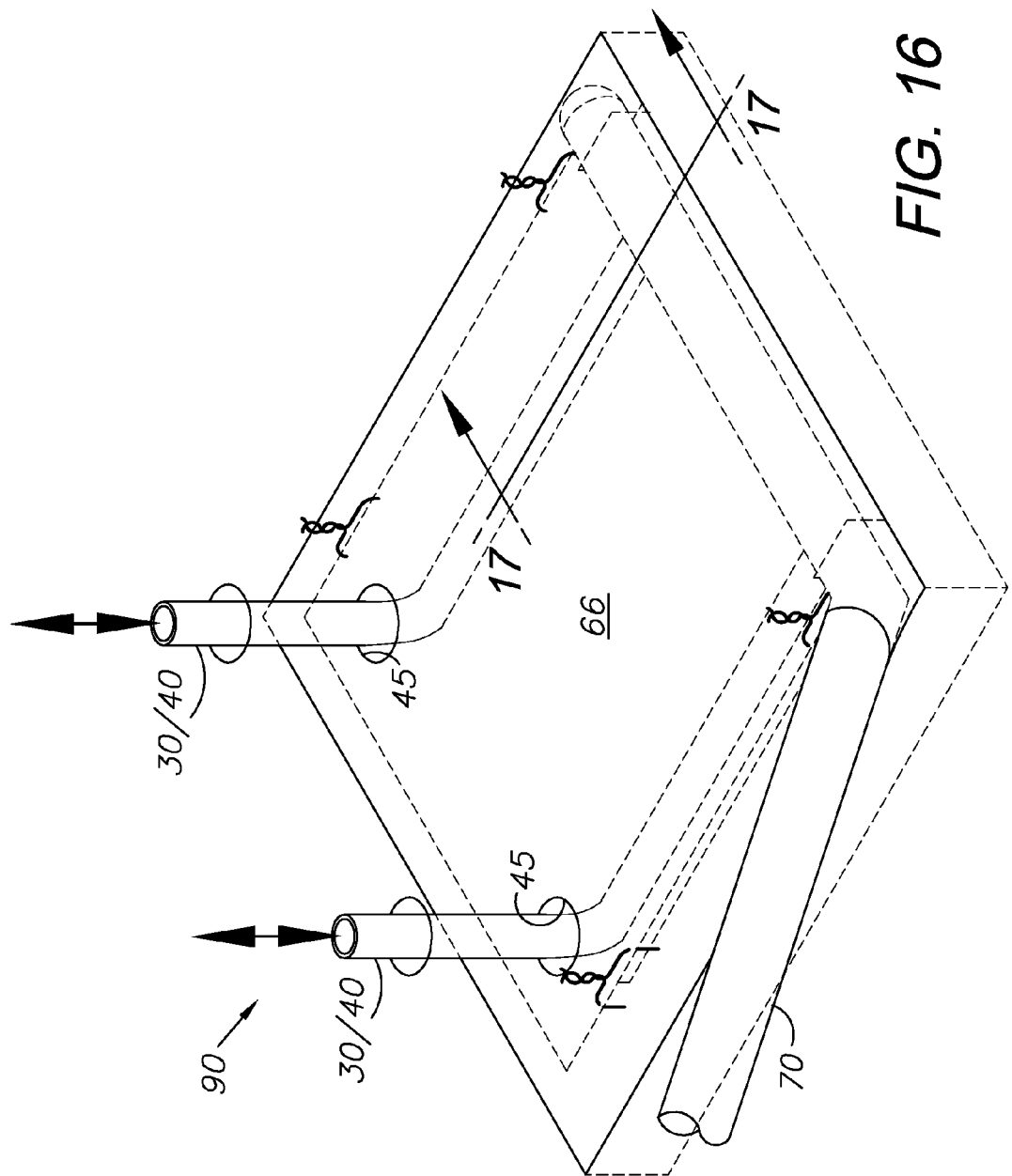
FIG. 16 shows another alternative aspect of the present invention with inflow/outflow conduits extending into the therapy zone.

Inflow and outflow conduits 30, 40 are inserted through openings 45 in the tissue flap plate 94 as shown in FIG. 16 and can underlie the scaffold 94. Alternatively, the flow conduits 30, 40 can be placed before the scaffolding 92 is placed. The tissue flap plate 94 can be formed in subcutaneous tissue, with the flow conduits 46, 48 extending through skin surface openings 98 and penetrating to an appropriate depth to reach the therapy zone 4. Alternatively, in a surface application the tissue flap plate 94 can comprise the dermal and epidermal layers.

Figure 17:
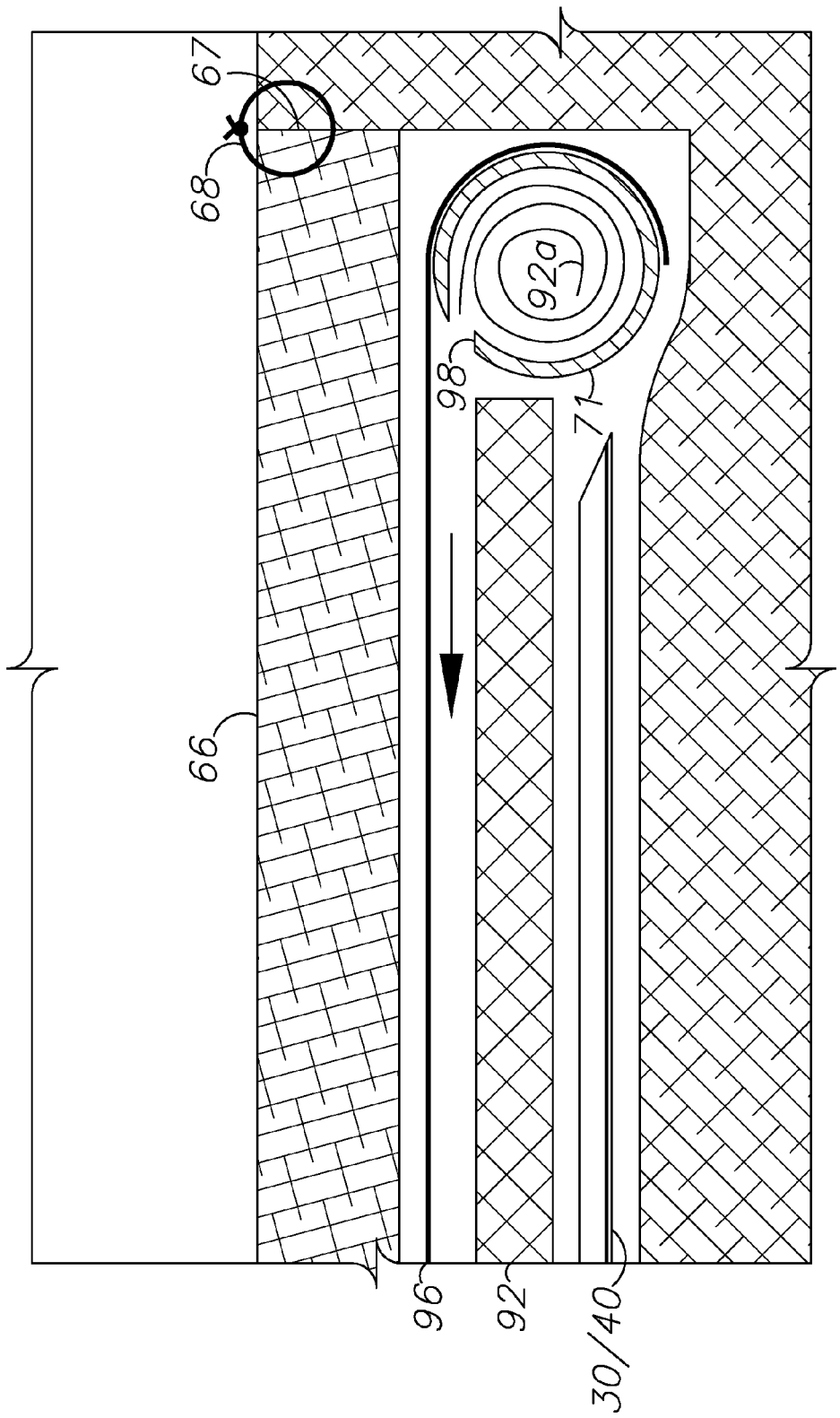
FIG. 17 is a cross-sectional view taken generally along line 17-17 in FIG. 16.

As shown in FIG. 17, the hemostatic fabric layer 96 can be wrapped around the endotube 52 for placement over the scaffolding 92. The endotube 52 can be slotted at 98 for accessing the lumen 53, which can receive the scaffolding 92 in a compression-rolled configuration 92a for unrolling into the therapy zone 4, for example, by a flexible rod extending through the endotube 52 for twisting externally to the patient.

Figure 18:
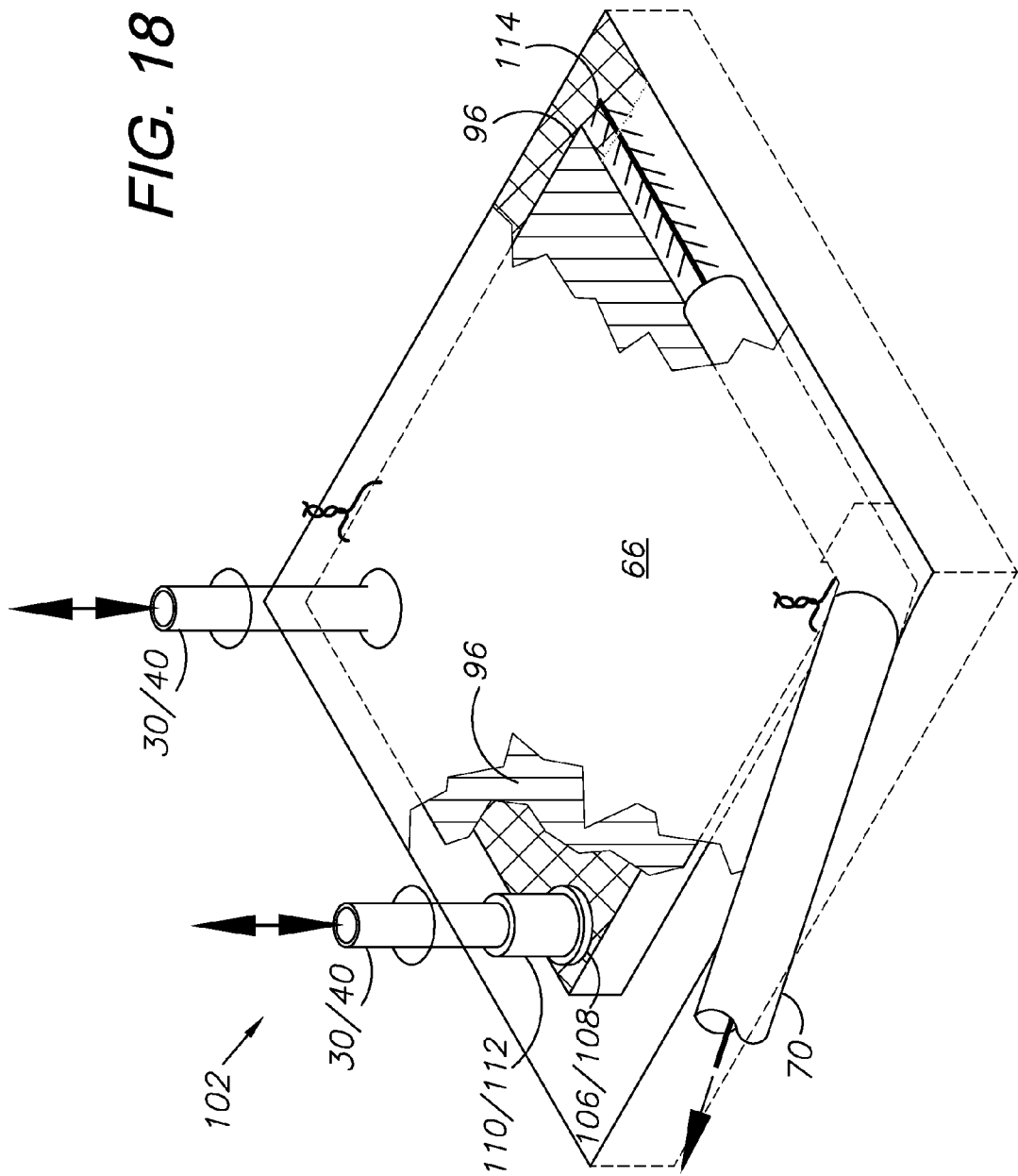
FIG. 18 shows another alternative aspect of the present invention with scaffolding located in the therapy zone including couplings.

FIG. 18 shows a cellular control system 102 comprising another modified aspect of the invention and including scaffolding 104 with inflow and outflow female couplings 106, 108, which connect to the inflow and outflow conduits 30, 40 respectively via male couplings 110, 112. A barbed-strand, self-anchoring surgical suture 114 is shown being extended into the therapy zone 4 from the endotube 52. Such sutures are available from Quill Medical, Inc. of Research Triangle Park, N.C. See, for example, U.S. Pat. No. 7,056,331, which is incorporated herein by reference. The endotube 52 facilitates inserting the barbed suture 114 and "setting" its prongs by tugging on the outer end extending from the endotube 52 external to the patient for self-anchoring the suture 114.

Figure 19:
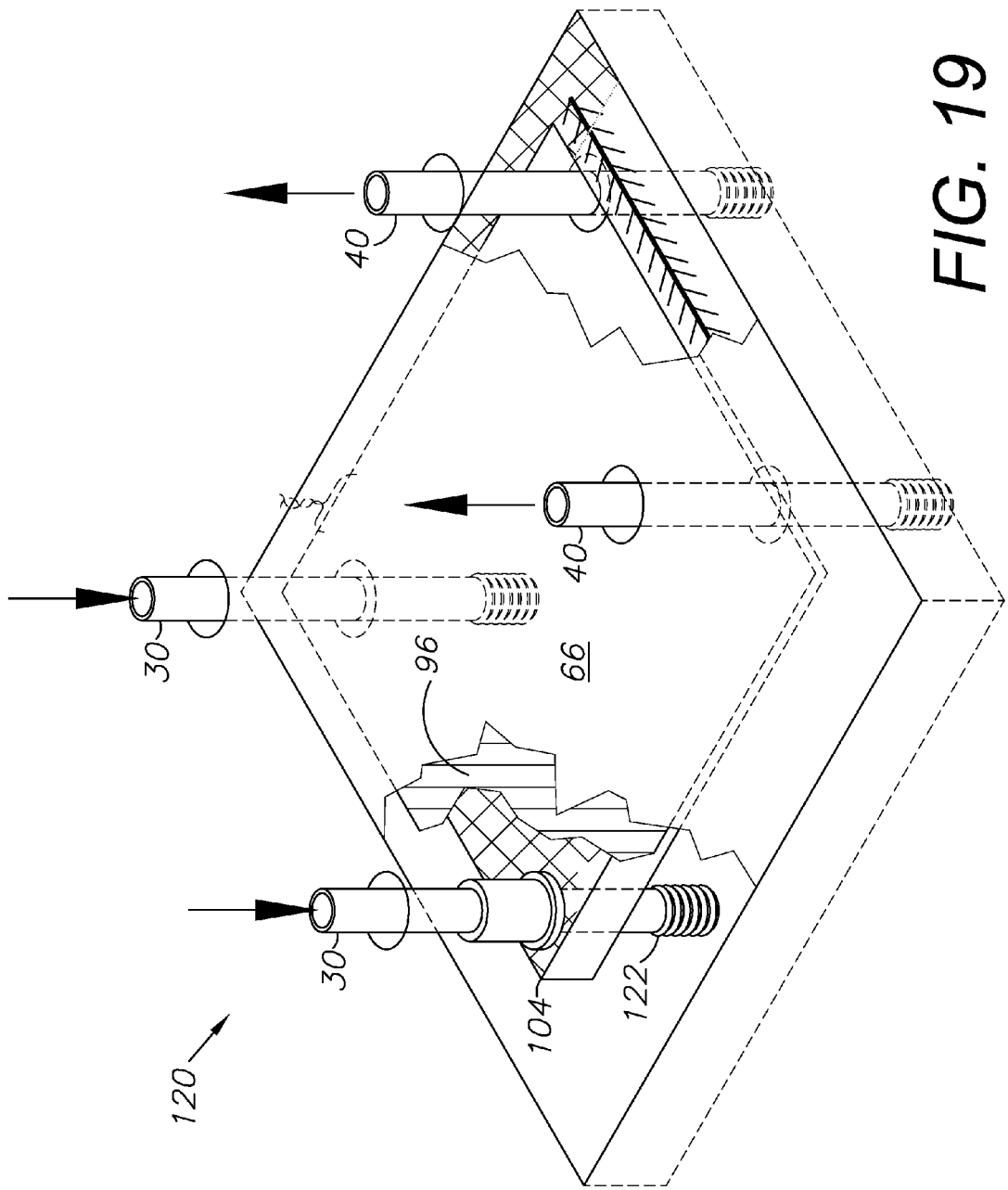
FIG. 19 shows another aspect of the invention with multiple bellows-type pumps or pillars in the therapy zone.

FIG. 19 shows a cellular control system 120 comprising another modified aspect of the present invention and including multiple bellows-action pillars 122 located below the scaffold 104 and fluidly connected to the inflow and outflow conduits 30, 40 respectively. The pillars 122 can reciprocably compress and expand in response to various pressures associated with the therapy zone 4. Such pressures can be externally-generated, e.g., by one or more of the factors 12, or internal pressures generated by the patient. Such pillars 122 can facilitate a "pumping" action with the cellular control system 120 by alternately expanding and contracting in order to move fluid into and out of the therapy zone 4.

Figure 20:
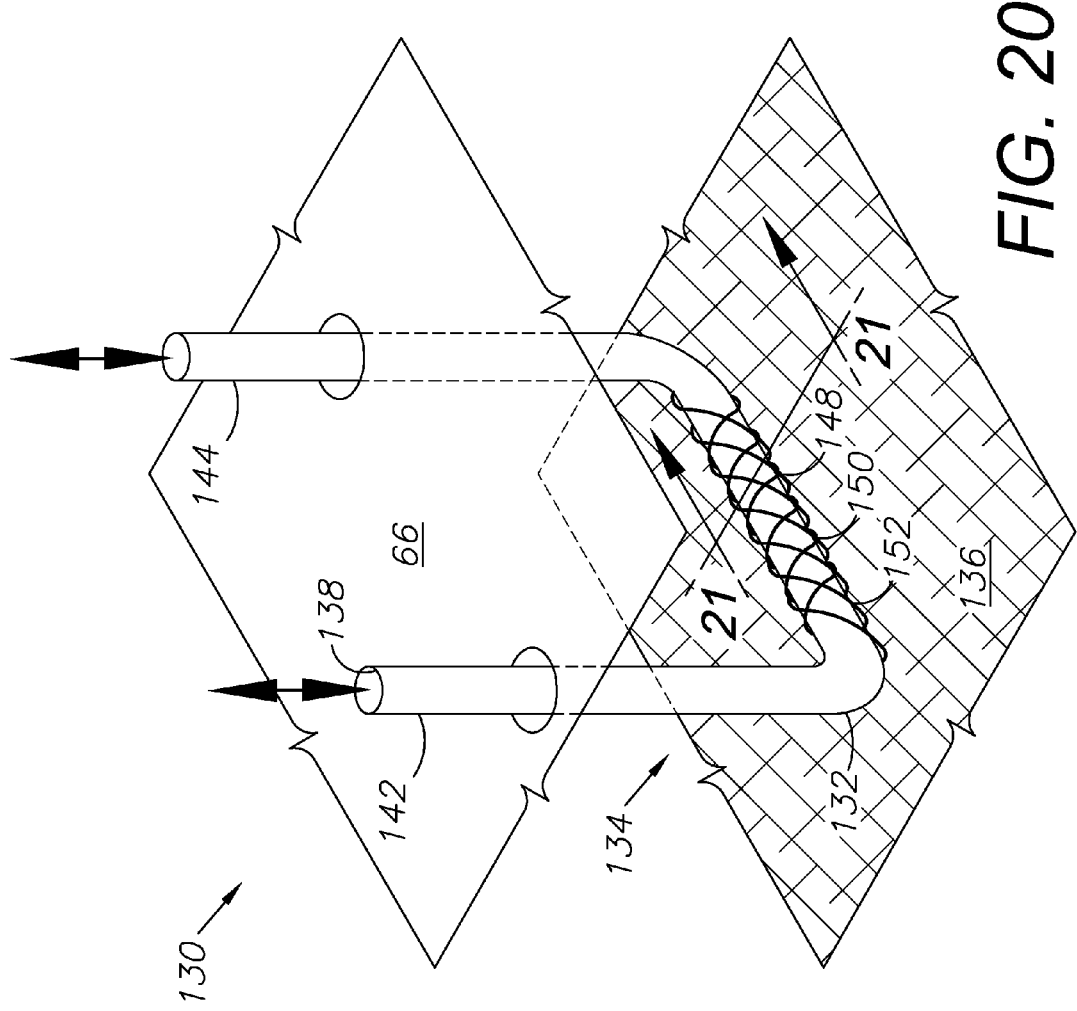
FIG. 20 shows another aspect of the invention with a closed-loop endotube assembly in the therapy zone.
Figure 21:
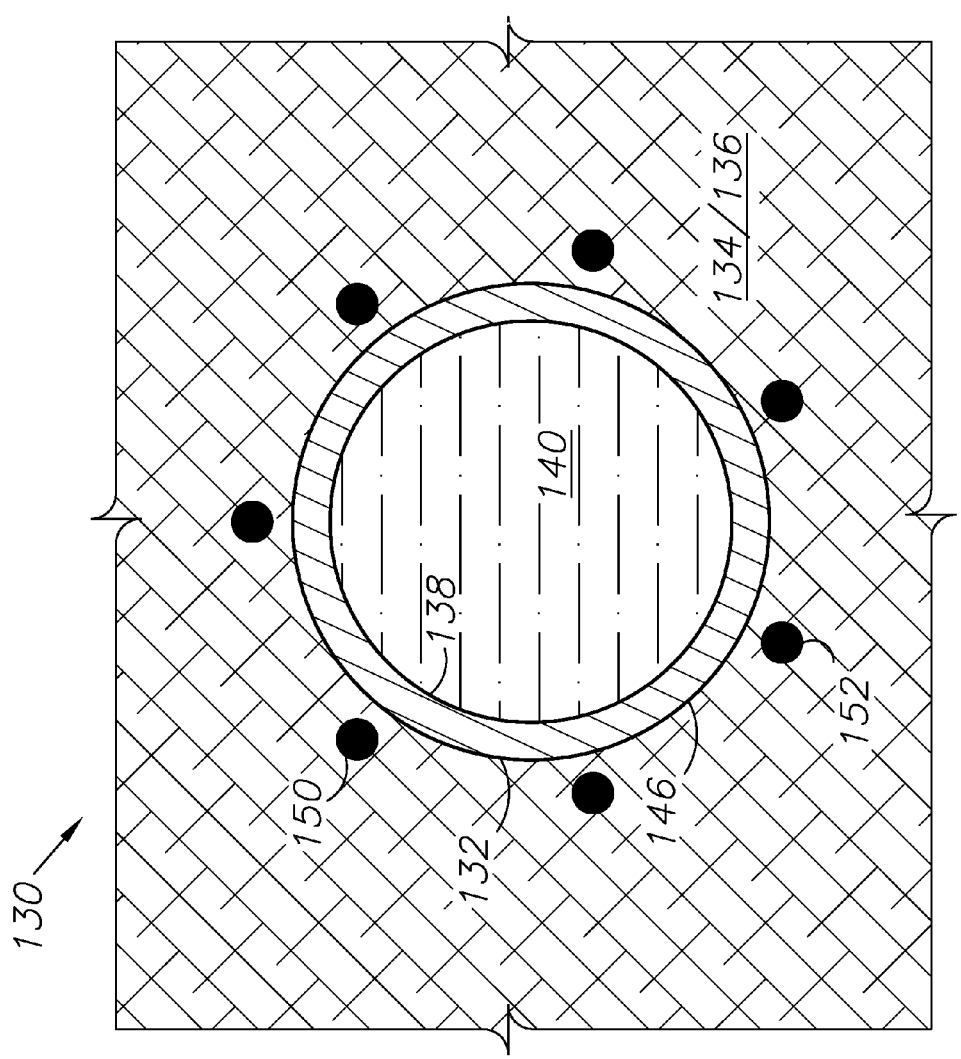
FIG. 21 is a cross-sectional view taken generally along line 21-21 in FIG. 20.

FIGS. 20 and 21 show a cellular control system 130 with a continuous loop endotube 132 forming the scaffolding 26 within a therapy zone 134 generally formed along the path of the endotube 132 through tissue 136. The endotube 132 includes a lumen 138, which can function as a conduit for introducing pharmacological and other substances 140, and/or extracting fluid from the patient. For example, the endotube 132 can be preloaded with cells for seeding the therapy zone 134. The endotube 132 forms inflow and outflow conduits 142, 144 with interchangeable functions. The endotube 132 includes an outer contact surface 146, which is adapted for engaging the tissue 136. The endotube 132 can be bioabsorbable, permanently implanted or extracted after completing a procedure. Moreover, the endotube 132 can be fabricated from a wide range of suitable materials chosen for compatibility with the therapeutic objectives of particular procedures. For example, semi-permeable materials can form pressure differentials and selectively transfer fluids. The endotube 132 can be perforated or slotted for fluid collection or dispersal. The external conduits 142, 144 can be connected to negative and/or positive pressure sources external to the therapy zone 134. Placement of the endotube 132 can be accomplished with a Trocar instrument, by surgical incision or placement under a tissue flap or trapdoor 66.

An open mesh 148 comprising a matrix of threads or capillary-type tubes 150 forms a cellular control sleeve 152 over an endotube outer contact surface 146. The mesh 148 can introduce cells, facilitate cellular ingrowth, channel fluid evacuation, enhance tissue contact interaction and otherwise facilitate the treatment objectives. The range of suitable materials includes bioabsorbable materials, pharmacological release materials (e.g., antibiotics, growth factors, antiseptics, imaging materials and other suitable materials) and hollow tubes for communicating fluids. The mesh 148 can be extracted with the endotube 132, or left in place after extraction. Still further, the mesh 148 can comprise closure members, such as the barbed suture strands 114 available from Quill Medical, Inc., which are described above.

The tubular or thread configuration shown in FIGS. 20 and 21 includes the system and method embodiments described above, with their components formed in tubular shapes. These embodiments can include conduit size components (cm to mm range diameters), capillary size (mm range diameters) and nano size (micron diameters). Length can generally be any suitable length. The endotubes 132 can be fabricated and installed in various configurations, including straight, linearly-connected (series), parallel configurations, spiral, coil, circular, wave-like, etc. with the intention of optimizing recipient tissue bed positioning and ease of installation. Installation can be accomplished manually by palpation, visually, with imaging techniques, endoscopically assisted or using open surgical techniques. Manipulative factors 12 can be introduced or applied, typically at one or both ends of the conduits 142, 144 with external (percutaneous) connections of the tubes, conduits or threads. The outer barrier or sheath of the tube (equivalent to the plate described above) and the makeup of the inner core (equivalent to the scaffolding described above) depend on the therapy intentions and the method of introduction, including placement, manipulation and control. With the system in a tubular configuration, the outer barrier is also the contact layer.

The tube can be placed in solid tissue, such as muscle or the liver using imaging techniques with a series of guide wires, followers and dilators, similarly to techniques for endovascular access. In long muscles such as the quadriceps, both entrance and exit areas are more feasible and more easily accomplished with a single guide wire or thin trocar. Input and output can thus be provided at opposite poles as the simplest and most efficient system for fluid manipulation. For example, in the liver, without open or endoscopic assistance, a single external conduit could serve as both input and output ports by alternating the functions or by use as a conduit carrying side-by-side smaller input/output lines that would travel in a preconfigured fashion through the outer sheath and inner core whereby the input would be instilled at one end and the output would be withdrawn from the opposite end and these functions could travel side-by-side in the single conduit separately contained.

Once the tube, conduit or thread has been placed, a series of rinses alternating with suction would be instituted to clear the space of the debris of the trauma of placement and to draw the surrounding tissue tightly against the thread and then to stimulate neovascular ingrowth to start. The outer sheath could have a pore size sufficient to be able to remove the blood and cell damage from placement. This could take an estimated one to two days or until the effluent is clear. The cell seeding then starts and is continued until it also comes out the effluent. The inner core is a scaffolding material that is biodegradable and chosen for its affinity to the cells to be seated. The outer sheath is in removed and the inner core, now seeded with cells, is left in place to grow and "take" as a graft of bioengineered tissue grown in-situ. If a single port is used, the inner core can be cut below the skin line and allowed to retract. If a double (2-ended) port is used, the output port is cut below the skin line and the outer sheath is then pulled out through the outer port. If the core is in the port, it is also cut off below the skin and allowed to retract. The end result is that the nonabsorbable outer sheath is removed and the absorbable scaffolding is left in a subcutaneous (inter-tissue) position.

Figure 22:
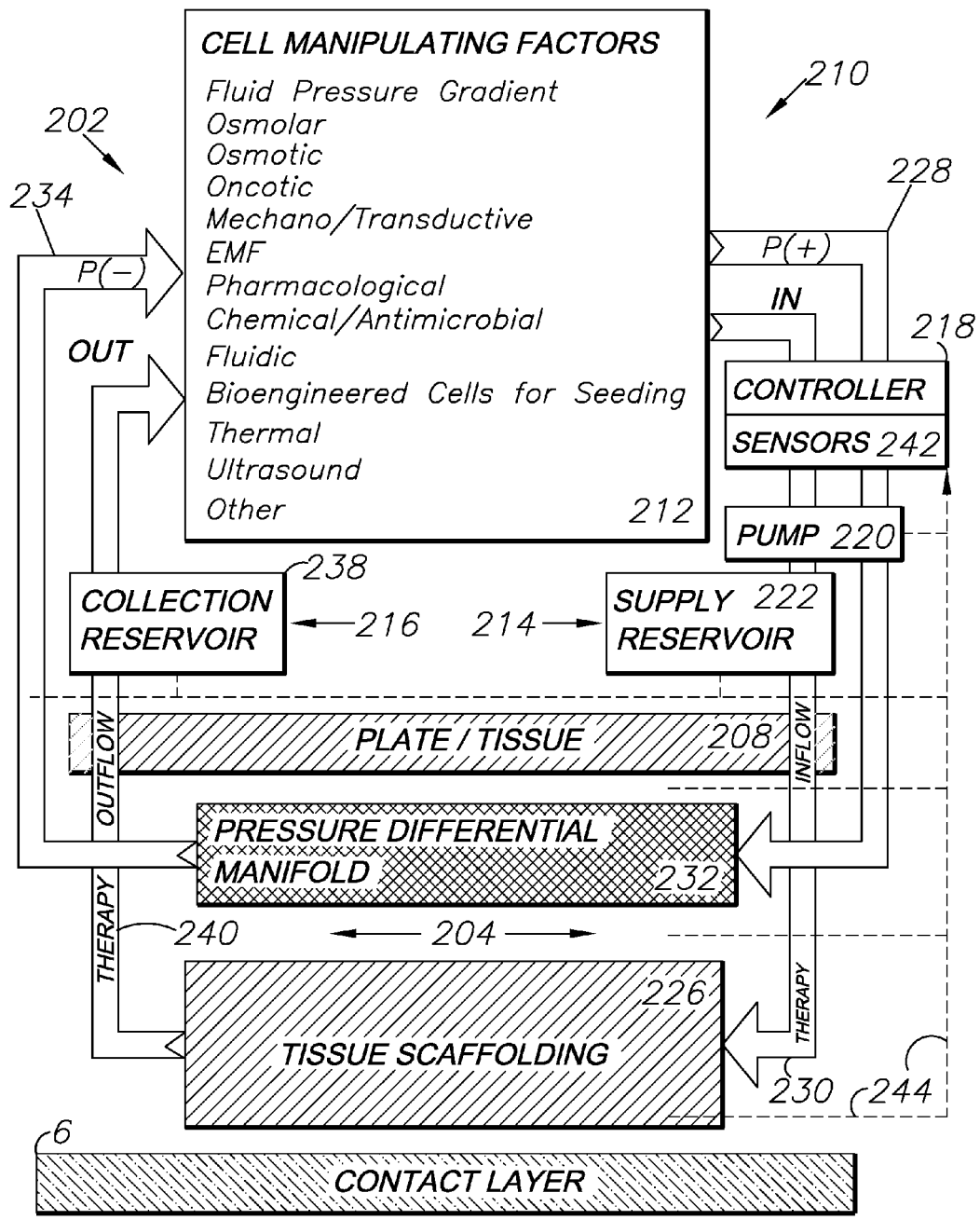
FIG. 22 is a schematic diagram similar to FIG. 1 showing another tissue regeneration and cellular control system embodying an alternative aspect of the present invention.

FIG. 22 shows a modified control system 202 comprising an alternative aspect of the present invention. The system 202 includes an inter-tissue space/therapy zone 204, which also defines a flow layer(s) for fluids generated internally and/or introduced externally. The tissue contact layer 6 can be located anywhere appropriate for treatment with the systems 2 and 202, including subdermal, subcutaneous, externally and internally; and in or on body cavities, organs, muscle fibers, ligamentous and osseous (skeletal) structure, etc. A plate/tissue component 208 can comprise a physical structure, such as a biocompatible material adapted for placement in or on the therapy zone 204. Alternatively, the component 208 can comprise a patient's tissue layer, such as the dermis, epidermis, etc. Functionally the component 208 cooperates with a pressure differential manifold 232 to facilitate and direct the flow of fluid, microbial agents, medications, irrigation, and other substances in the therapy zone 204. Either or both of the tissue scaffolding 226 and the pressure differential manifold 232 can comprise cellular matrices, synthetic tissue, living tissue or derivatives of living tissue.

The system 202 can include a variety of configurations with the plate/tissue component 208 cooperating with the manifold 232 and scaffolding 226 to form the pressure differential zone 204. Fluid pulse waves can be introduced to the therapy zone 204 by cycling a pump 220 with a controller 218 and pulsing fluid through various tubing and manifold configurations, including those shown in FIGS. 2-21. A sensor suite 242 is connected to the controller 218 and can include multiple sensor suite feeds 244 extending to various components and areas of the therapy zone 204. The sensor suite 242 can include sensors for monitoring various operating parameters, including pressure, temperature, microbial activity, chemical composition (e.g., oxygen and $CO_2$ levels), etc. Sensor inputs to the controller 218 can be digitized for processing by the microprocessor controller 218. The sensor signal input information can be utilized by the controller 218 for controlling various operating parameters of the system 202, such as the pump 220, the inflow/outflow lines 230/240 and the factor source 212.

The tubing and manifold elements shown therein can be rearranged and reconfigured as necessary to achieve a wide range of alternative systems for accommodating various patient conditions and treatment objectives.

Relatively small-amplitude pressure changes of, for example, a few mm Hg, can be sufficient for achieving desired therapeutic results. More specifically, such pressure changes can stimulate cellular activity, reepithelialization, cell migration, regeneration and other physiological changes associated with the healing process. Alternatively or additionally, components of the system 202, such as the bellows-equipped pillars 122 shown in FIG. 19, can provide or supplement such pressure waves, for example with the blood pressure cycles of the circulatory system or similar pressure-varying, dynamic physiological functions, such as musculature, lymphatic, respiratory, etc. The system 202 can thus operate using the dynamic pulsations naturally occurring in-vivo, and/or with externally-applied forces, such as the pump 220.

In addition the to in-vivo systems and methodologies described herein, the system 202 is adaptable for benchtop, tissue culture, tissue engineering, ex-vivo and other applications for a wide range of research, bioengineering, tissue culture and other useful applications, which share a common element of cellular control and manipulation.

A general interface 210 can comprise a wide range of suitable component/patient interface constructions, such as internal/external dressings, closure screens, etc. For examples, see Zamierowski U.S. Pat. No. 4,969,880; U.S. Pat. No. 5,100,396; U.S. Pat. No. 5,261,893; U.S. Pat. No. 5,527,293; and U.S. Pat. No. 6,071,267; and U.S. Patent Publications No. 2008/0228221 and No. 2008/0228222, which are incorporated herein by reference. An exemplary list of cell manipulating factors as shown at 212 for application to the therapy zone 204 via the interface 210, and is not to be construed as limiting. Various other cell manipulating factors can be employed for achieving desired therapeutic and other beneficial results. On a supply/input side 214 of the system 202, a controller 218 can be provided for preprogramming to control various components and operating parameters of the system 202, such as a pump 224 for delivering fluids and other factors from the source 212 to the pressure differential manifold 232 via inlet lines 228 and to tissue scaffolding 226 via therapy inflow input lines 230. Likewise on the outlet side 216, line 234 is connected to the pressure differential manifold 232 and returns to the source 212. The therapy outflow line 240 is connected to the tissue scaffolding 226 and returns to the source 212.

An optional supply reservoir 222 can be connected to the therapy inflow line 230 and can provide a secondary or alternative source of pharmacological and other factors for input to the therapy zone 204 via the therapy inflow line 230. A corresponding collection reservoir 238 can receive fluid from the therapy zone 204 via the therapy outflow line 240. Of course, collected waste fluid can be disposed of using established medical waste disposal procedures.

These systems 2 and 202 shown and described above comprise exemplary aspects of the invention, which may be embodied in various other forms. For example, the planar orientations of the system components can be rearranged and reconfigured in-situ as determined by the medical practitioner. Alternative orientations can include inverted, vertical, horizontal, etc. Moreover, the orientations discussed above are for illustration and could vary depending upon the position of the patient. Still further, the pressure differential manifold 232 could be formed within or below the tissue scaffolding 226 and in various spatial relationships to the plate/tissue 208. The component configurations can assume any appropriate configuration, such as tubular, spiral, circular, etc.

It is to be understood that while certain aspects and embodiments of the invention are described and shown, the invention is not limited thereto and can assume a wide range of other, alternative aspects and embodiments.

The invention claimed is:

1. A medical cellular control system for a tissue therapy zone, which system comprises:
   a cell manipulating factor source;
   a plate adapted to be located in the therapy zone;
   a pressure differential manifold adapted to be positioned in proximity to the plate and adapted to be located in the therapy zone;
   a therapy inflow line adapted for connection to the factor source and to the pressure differential manifold;
   said therapy inflow line being adapted for supplying a factor from said factor source to said pressure differential manifold;
   a tissue scaffolding component adapted to be located in the therapy zone and adapted for fluidic connection to said factor source via the pressure differential manifold and the inflow line;
   an endotube adapted for fluidic connection to the therapy zone and the factor source;
   a flexible cover furled around the endotube; and
   said flexible cover having a retracted position and a covering position and being extendable from said endotube from said retracted position to said covering position over said tissue scaffolding component.

2. The system according to claim 1 wherein said plate comprises in-situ tissue or an inert, biocompatible material and is adapted for containing pressure and directing fluid flow in said therapy zone.

3. The system according to claim 1 wherein said factors are chosen from the group comprising: fluid pressure gradient; osmolar; osmotic; oncotic; mechano/transductive; electromagnetic field (EMF); pharmacological; chemical/antimicrobial; fluidic; bioengineered cells for seeding; thermal; and ultrasound.

4. The system according to claim 1, which includes:
   a pump adapted for connection to the factor source and the inflow line; and
   a controller adapted for connection to the pump and adapted for controlling the operation of the pump in response to therapy zone conditions.

5. The system according to claim 1, which includes:
   a manifold including a fluid-permeable foam material; and
   manifold tubing adapted for fluidic connection to the foam material and to the inflow line and an outflow line.

6. The system according to claim 1, which includes:
   a barbed surgical suture within said endotube; and
   said barbed surgical suture having an engaged position extending from said endotube into said therapy zone.

7. The system according to claim 1, which includes:
   an inflow manifold adapted for connection to said inflow line;
   said inflow manifold being adapted for connection to said therapy zone and distributing a cellular control factor therein;
   an outflow manifold adapted for connection to said outflow line; and
   said outflow manifold being adapted for connection to said therapy zone and extracting fluid from said therapy zone.

8. The system according to claim 7, which includes:
   said inflow and outflow manifolds including multiple manifold branches extending from respective inflow and outflow lines to multiple locations in said therapy zone.

9. The system according to claim 1, which includes:
   multiple sutures or clips adapted for anchoring said scaffolding to a fluid bed in said therapy zone.

10. The system according to claim 1, which includes a pulse wave generator adapted for generating a pulse wave in said therapy zone via said inflow tubing.

11. The system according to claim 1, which includes said therapy zone being configured for applying a pulse-wave with in-vivo pressure differential from a circulatory, lymphatic or respiratory system.

12. A medical cellular control system for a tissue therapy zone, which system comprises:
    a cell manipulating factor source;
    a plate adapted to be located in the therapy zone;
    a pressure differential manifold adapted to be positioned in proximity to the plate and adapted to be located in the therapy zone;
    a therapy inflow line adapted for connection to the factor source and to the pressure differential manifold;
    said therapy inflow line being adapted for supplying a factor from said factor source to said pressure differential manifold;
    a tissue scaffolding component adapted to be located in the therapy zone and adapted for fluidic connection to said factor source via the pressure differential manifold and the inflow line;
    an endotube adapted for fluidic connection to the therapy zone and the factor source;
    a barbed surgical suture within said endotube; and
    said barbed surgical suture having an engaged position extending from said endotube and adapted to extend into said therapy zone.

13. The system according to claim 12, which includes:
    a flexible cover adapted to be furled around the endotube; and
    said flexible cover having a retracted position and a covering position and being extendable from said endotube from said retracted position to said covering position over said tissue scaffolding component.

* * * * *